US 9,808,544 B2

(12) United States Patent
Cooper et al.

(10) Patent No.: US 9,808,544 B2
(45) Date of Patent: *Nov. 7, 2017

(54) ULTRAVIOLET LIGHT TREATMENT CHAMBER

(75) Inventors: James Randall Cooper, San Diego, CA (US); Richard May, San Diego, CA (US)

(73) Assignee: Ultraviolet Sciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/416,075

(22) Filed: Mar. 31, 2009

(65) Prior Publication Data

US 2010/0078574 A1    Apr. 1, 2010

Related U.S. Application Data

(63) Continuation-in-part of application No. 11/959,445, filed on Dec. 18, 2007, and a continuation-in-part of
(Continued)

(51) Int. Cl.
*B01J 19/12*    (2006.01)
*A61L 2/00*    (2006.01)
(Continued)

(52) U.S. Cl.
CPC .............. *A61L 2/0047* (2013.01); *A61L 9/205* (2013.01); *A61M 1/3681* (2013.01);
(Continued)

(58) Field of Classification Search
CPC ...... A61L 2/0047; A61L 9/205; A61L 2/0094; A61L 2202/22; A61L 2209/211;
(Continued)

(56) References Cited

U.S. PATENT DOCUMENTS 2,072,416 A    3/1937    Berndt et al.
2,072,417 A    3/1937    Berndt et al.
(Continued)

FOREIGN PATENT DOCUMENTS

CA    2757285    10/2010
CN    1537001    10/2004
(Continued)

OTHER PUBLICATIONS

PCT International Search Report and Written Opinion of the International Searching Authority from PCTUS0631643 dated Jan. 16, 2008.
(Continued)

*Primary Examiner* — Xiuyu Tai
(74) *Attorney, Agent, or Firm* — Fitch, Even, Tabin & Flannery LLP

(57) ABSTRACT

An apparatus for the treatment of a liquid that includes a chamber having at least one inner surface, the chamber adapted for passage of a fluid therethrough. The chamber is at least 80 percent enclosed. The apparatus also includes an optional ultraviolet-transmissive tube disposed within the chamber and also adapted for the passage of the liquid therethrough. The apparatus further includes an ultraviolet lamp disposed within the chamber and, optionally, within the ultraviolet-transmissive tube. A reflective material is interposed between the chamber and the transmissive tube. The reflective material is adapted so as to reflect at least a portion of light emitted by the ultraviolet lamp, wherein the reflective material is at least 80 percent reflective.

15 Claims, 8 Drawing Sheets

Related U.S. Application Data application No. 11/217,772, filed on Aug. 31, 2005, now Pat. No. 7,511,281.

(51) Int. Cl.
*A61L 9/20* (2006.01)
*A61M 1/36* (2006.01)
*C02F 1/32* (2006.01)
*C02F 1/28* (2006.01)
*C02F 1/42* (2006.01)
*C02F 1/44* (2006.01)

(52) U.S. Cl.
CPC ........... *B01J 19/123* (2013.01); *B01J 19/124* (2013.01); *C02F 1/325* (2013.01); *A61L 2/0094* (2013.01); *A61L 2202/22* (2013.01); *A61L 2209/211* (2013.01); *A61L 2209/212* (2013.01); *A61M 2205/053* (2013.01); *B01J 2219/0877* (2013.01); *C02F 1/283* (2013.01); *C02F 1/42* (2013.01); *C02F 1/441* (2013.01); *C02F 2201/003* (2013.01); *C02F 2201/328* (2013.01); *C02F 2201/3223* (2013.01); *C02F 2201/3228* (2013.01)

(58) Field of Classification Search
CPC .. A61L 2209/212; A61L 2/10; A61M 1/3681; A61M 2205/053; B01J 19/123; B01J 19/124; C02F 1/325; C02F 1/283; C02F 1/42; C02F 1/441; C02F 2201/003; C02F 2201/3223; C02F 2301/206; C02F 2301/024; C02F 2201/3221; C01B 13/10; F24F 2003/1667; A23L 3/28
USPC ...................................................... 422/186.3
See application file for complete search history.

(56) References Cited

U.S. PATENT DOCUMENTS

| | | |
|---|---|---|
| 2,482,507 A | 9/1949 | Rentschler et al. |
| 3,569,754 A | 3/1971 | Priebe et al. |
| 3,572,391 A | 3/1971 | Hirsch |
| 3,814,680 A | 6/1974 | Wood |
| 3,923,663 A | 12/1975 | Reid |
| 3,941,670 A | 3/1976 | Pratt |
| 3,959,504 A | 5/1976 | Grufstedt |
| 4,008,045 A | 2/1977 | Free |
| 4,042,325 A | 8/1977 | Tensmeyer |
| 4,042,850 A | 8/1977 | Ury et al. |
| 4,112,335 A | 9/1978 | Gonser |
| 4,141,686 A | 2/1979 | Lewis |
| 4,207,541 A | 6/1980 | Karger et al. |
| 4,232,276 A | 11/1980 | Iwata |
| 4,304,996 A | 12/1981 | Blades |
| 4,327,276 A | 4/1982 | Injushin et al. |
| 4,336,223 A | 6/1982 | Hillman |
| 4,400,270 A | 8/1983 | Hillman |
| 4,469,835 A | 9/1984 | Laurin |
| 4,507,587 A | 3/1985 | Wood et al. |
| 4,534,282 A | 8/1985 | Marinoza |
| 4,535,247 A | 8/1985 | Kurtz |
| 4,601,822 A | 7/1986 | Zamburro |
| 4,643,464 A | 2/1987 | Weinhold |
| 4,766,321 A | 8/1988 | Lew et al. |
| 4,769,131 A | 9/1988 | Noll et al. |
| 4,786,812 A | 11/1988 | Humphreys |
| 4,831,268 A | 5/1989 | Fisch et al. |
| 4,866,282 A | 9/1989 | Miripol et al. |
| 4,871,559 A | 10/1989 | Dunn et al. |
| 4,887,008 A | 12/1989 | Wood |
| 4,887,192 A | 12/1989 | Simpson et al. |
| 4,902,411 A | 2/1990 | Lin |
| 4,919,951 A | 4/1990 | Jensen et al. |
| 4,948,980 A | 8/1990 | Wedekamp |
| 4,971,687 A | 11/1990 | Anderson |
| 5,023,460 A | 6/1991 | Foster, Jr. et al. |
| 5,037,618 A | 8/1991 | Hager |
| 5,048,404 A | 9/1991 | Bushnell |
| 5,069,782 A | 12/1991 | Moyher, Jr. |
| 5,120,450 A | 6/1992 | Stanley, Jr. |
| 5,151,252 A | 9/1992 | Mass |
| 5,208,461 A | 5/1993 | Tipton |
| 5,227,637 A | 7/1993 | Herold et al. |
| 5,230,792 A | 7/1993 | Sauska et al. |
| 5,235,905 A | 8/1993 | Bushnell et al. |
| 5,247,178 A | 9/1993 | Ury et al. |
| 5,288,647 A | 2/1994 | Zimlich, Jr. et al. |
| 5,302,356 A | 4/1994 | Shadman et al. |
| 5,393,541 A | 2/1995 | Bushnell et al. |
| 5,395,591 A | 3/1995 | Zimlich, Jr. et al. |
| 5,446,289 A | 8/1995 | Shodeen et al. |
| 5,447,733 A | 9/1995 | Bushnell et al. |
| 5,451,367 A | 9/1995 | Stark et al. |
| 5,489,442 A | 2/1996 | Dunn et al. |
| 5,498,394 A | 3/1996 | Matschke |
| 5,573,666 A | 11/1996 | Korin |
| 5,597,482 A | 1/1997 | Melyon |
| 5,626,768 A | 5/1997 | Ressler et al. |
| 5,658,530 A | 8/1997 | Dunn |
| 5,686,789 A | 11/1997 | Schoenbach |
| 5,768,853 A | 6/1998 | Bushnell |
| 5,786,598 A | 7/1998 | Clark et al. |
| 5,814,523 A | 9/1998 | Zimlich, Jr. et al. |
| 5,843,309 A | 12/1998 | Mancil |
| 5,900,211 A | 5/1999 | Dunn et al. |
| 5,916,439 A | 6/1999 | Oleskow |
| 5,925,885 A | 7/1999 | Clark et al. |
| 5,939,829 A | 8/1999 | Schoenbach |
| 6,013,918 A | 1/2000 | Bushnell |
| 6,027,754 A | 2/2000 | Bushnell et al. |
| 6,030,578 A | 2/2000 | McDonald |
| 6,045,845 A | 4/2000 | Gundt |
| 6,054,097 A | 4/2000 | Mass et al. |
| 6,072,273 A | 6/2000 | Schoenbach |
| 6,083,387 A | 7/2000 | Le Blanc et al. |
| 6,087,783 A | 7/2000 | Eastlund et al. |
| 6,110,423 A | 8/2000 | Bushnell et al. |
| 6,150,663 A | 11/2000 | Rosenthal |
| 6,190,609 B1 | 2/2001 | Chapman et al. |
| 6,228,332 B1 | 5/2001 | Dunn et al. |
| 6,312,931 B1 | 11/2001 | O'Dwyer et al. |
| 6,346,770 B1 | 2/2002 | Schoenbach |
| 6,433,344 B1 | 8/2002 | Salisbury et al. |
| 6,566,659 B1 | 5/2003 | Clark et al. |
| 6,589,489 B2 | 7/2003 | Morrow et al. |
| 6,614,039 B2 | 9/2003 | Hollander |
| 6,730,923 B1 | 5/2004 | May et al. |
| 6,849,233 B2 | 2/2005 | Bushnell et al. |
| 7,038,219 B2 | 5/2006 | Clark et al. |
| 7,091,495 B2* | 8/2006 | Panico et al. ............ 250/432 R |
| 7,511,281 B2 | 3/2009 | Cooper |
| 2002/0043504 A1* | 4/2002 | Chen et al. .................. 210/748 |
| 2002/0103409 A1 | 8/2002 | Kuriyama |
| 2002/0119072 A1 | 8/2002 | Bushnell et al. |
| 2002/0168305 A1 | 11/2002 | Morrow et al. |
| 2002/0176796 A1 | 11/2002 | Holoway et al. |
| 2003/0030011 A1 | 2/2003 | Brown et al. |
| 2003/0060747 A1 | 3/2003 | Fries et al. |
| 2003/0147770 A1 | 8/2003 | Brown et al. |
| 2004/0004044 A1 | 1/2004 | Anderson |
| 2004/0144733 A1 | 7/2004 | Cooper |
| 2004/0166018 A1 | 8/2004 | Clark |
| 2005/0109690 A1 | 5/2005 | Bechtold |
| 2005/0115498 A1 | 6/2005 | Ingram et al. |
| 2005/0264236 A1 | 12/2005 | Lloyd et al. |
| 2007/0045561 A1 | 3/2007 | Cooper |

FOREIGN PATENT DOCUMENTS

| | | |
|---|---|---|
| CN | 2698348 | 5/2005 |
| CN | 1656595 | 8/2005 |
| CN | 2804073 | 8/2006 |

(56) References Cited

FOREIGN PATENT DOCUMENTS

| | | |
|---|---|---|
| DE | 845497 C | 7/1952 |
| DE | 19617467 | 11/1997 |
| EP | 0277505 A1 | 8/1988 |
| EP | 0277505 | 8/1999 |
| EP | 1069444 | 1/2001 |
| EP | 2485038 | 8/2012 |
| FR | 2879588 A1 | 6/2006 |
| JP | 48018200 | 3/1973 |
| JP | 49119441 | 10/1974 |
| JP | 50026255 | 3/1975 |
| JP | 51106236 | 8/1976 |
| JP | 58214388 | 12/1983 |
| JP | 02095585 | 7/1990 |
| JP | 03015692 | 2/1991 |
| JP | 06048882 | 7/1994 |
| JP | 06233979 | 8/1994 |
| JP | 07213643 | 8/1995 |
| JP | 08117741 | 5/1996 |
| JP | 2001500782 | 1/2001 |
| JP | 3141893 | 3/2001 |
| JP | 2001066422 | 3/2001 |
| JP | 2004-121577 | 10/2002 |
| JP | 200441222 | 2/2004 |
| JP | 2004121577 | 4/2004 |
| JP | 2005-52708 | 6/2005 |
| JP | 2005527953 | 9/2005 |
| JP | 2006-82085 | 3/2006 |
| JP | 2007-02200 | 2/2007 |
| JP | 2007533441 | 11/2007 |
| JP | 2008299094 | 12/2008 |
| JP | 2009508663 | 3/2009 |
| KR | 1020080042906 | 5/2008 |
| WO | 8706841 | 11/1987 |
| WO | 9714915 | 4/1997 |
| WO | 9950183 | 10/1999 |
| WO | 0078681 | 12/2000 |
| WO | WO2004050130 | 6/2004 |

OTHER PUBLICATIONS

Notice of Allowance for U.S. Appl. No. 11/217,772 dated Nov. 18, 2008.
"Water Disinfection with Ultraviolet Light", *Aquafine Wedeco Environmental Systems Inc.* 1996.
Bender, "Photolytic oxidation of contaminated water using a high-energy, pulsed ultra-violet flashlamp operating in the blackbody regime", *OSA Symposium* 1997, pp. 1-14.
Bolton, Jr., *Ultraviolet applications Handbook*, 2nd Edition 2001, Photosciences Inc. 2001, p. 37.
Cooper, U.S. Appl. No. 11/217,772.
Cooper, U.S. Appl. No. 11/959,445.
Dunn, "PureBright: Sterilization Using Intense Pulsed Light", *Summary of Presentation to International society of Pharmaceutical Engineers* Dec. 1995.
Jagger, "Introduction to Research in Ultraviolet Photo Biology", 1967, pp. 1-164.
Rentschler, "Bactericidal Effect of Ultraviolet Radiation", *Research Department, Westinghouse Lamp Division*, Bloomfield, New Jersey, pp. 745-774.
Office Action from U.S. Appl. No. 11/217,772 dated Jun. 25, 2008.
Zimmerman, "Electrical Breakdown, Electropermeabilization and Electrofusion", *Physiology Biochemistry Pharmacology.*, vol. 105 1986, pp. 176-256.
Landfill Systems, Aquafine Wedeco Environmental Systems, Inc., 1996.
Cooper, U.S. Appl. No. 11/217,772, filed Aug. 31, 2005.
Cooper, U.S. Appl. No. 11/959,445, filed Dec. 18, 2007.
Rentschler, "Bactericidal Effect of Ultraviolet Radiation", Research Department, Westinghouse Lamp Division, Bloomfield, New Jersey Oct. 26, 1940, pp. 745-774.
Bakthisaran, "The Application of UV Technology to Pharmaceutical Water Treatment", European Journal of Parenteral Sciences 3(4) Mar. 1998, pp. 97-102.
European Search Report for European App. No. 06801427.3 dated Nov. 19, 2009.
Examination Report from the European Patent Office for EP App. No. 06801427.3 dated Mar. 5, 2010.
International Search Report and Written Opinion of the International Searching Authority for PCT/US2008086305 dated Jun. 29, 2009.
International Search Report and Written Opinion of the International Searching Authority for PCT/US2010/029251 dated Nov. 26, 2010.
Non-Final Office Action for U.S. Appl. No. 11/959,445 dated Dec. 8, 2010.
Notice of First Office Action from the State Intellectual Property Office of the People's Republic of China for App. No. 200680036959.4 dated Oct. 21, 2010.
Notice of Rejection from the Japanese Patent Office for App. No. 2008529088 dated Feb. 8, 2011.
Office Action from the Mexican Patent Office in the Mexican Institute of Industrial Property for Mexican App. No. MXa2008003022 dated Aug. 19, 2010.
Office of Intellectual Property Australia, Examiner's First Report on App. No. 2006285220 dated Jan. 18, 2011.
Non-Final Office Action from U.S. Appl. No. 11/959,445 dated Jan. 9, 2013.
Notice of Allowance for Japanese Patent Application No. 2008-529088 mailed from the JPO dated Jan. 15, 2013.
Notice of First Office Action for China Patent Application No. 201080023548.8 mailed from the Patent Office of the China State Intellectual Property Office dated Dec. 28, 2012.
Communication Pursuant to Article 94(3) EPC for European Patent Application No. 12158784.4 dated May 3, 2013, 6 pages.
Final Office Action for Japanese Patent Application No. 2010-539632 mailed by the Japan Patent Office dated May 7, 2013, 5 pages.
Final office action from U.S. Appl. No. 11/959,445 dated May 20, 2013.
Extended European Search Report from European Application No. 10 762 191.4 mailed from the EPO dated Oct. 17, 2012.
Non-final rejection from Korean Patent Application No. 2008-7007426 mailed from Korean Intellectual Property Office dated Sep. 28, 2012.
Patent Examination Report No. 3 for Australian Patent Application No. 2006285220 mailed from the Australian Patent Office dated Oct. 11, 2012.
Australian Patent Application No. 2006285220, Ultraviolet Sciences, Inc. Notice of Acceptance dated Oct. 30, 2012, 3 pages.
Office Action from the Mexican Patent Office for Mexican Application No. MX/a/2010/006924 dated Jun. 18, 2011 (3 pgs.).
Patent Examination Report No. 1 from Australian Patent Application No. 2008338653 mailed from Australian Patent Office dated Feb. 5, 2013.
Extended European Search Report from 12158784.4 dated Jul. 5, 2012.
Final Office Action for U.S. Appl. No. 11/959,445 dated Jul. 26, 2011.
Notice of Final Decision of Rejection from the Japan Patent Office for Japanese Patent App. No. 2008-529088 dated Jun. 1, 2012.
Second Office Action from the State Intellectual Property Office of the People's Republic of China for App. No. 2006800369594 dated Nov. 8, 2011.
Decision on Rejection from the Patent Office of the State Intellectual Property Office of the People's Republic of China for Application No. 200680036959.4 dated Jul. 4, 2012.
Office Action for Japanese Patent Application No. 2010-539632 mailed by the Japanese Patent Office dated Jul. 31, 2012.
Patent Examination Report No. 2 for Patent Application No. 2006285220 issued by the Australian Patent Office dated Aug. 2, 2012.
Patent Abstracts for Japanese Publication No. 2004-121577 dated Apr. 22, 2004 with translation.

(56) References Cited

OTHER PUBLICATIONS

Patent Abstracts for Japanese Publication No. 07-213643 dated Aug. 15, 1995 with translation.
Notice on the Second Office Action for Chinese Patent Application No. 201080023548.8 mailed from the State Intellectual Property Office of the People's Republic of China dated Jul. 15, 2013.
First Office Action from Canadian Patent Application 2,620,780 mailed from the Canadian Intellectual Property Office dated Oct. 18, 2013.
Extended European Search Report from European Application No. 08860955.7 dated Oct. 16, 2013.
Communication on Reexamination for Chinese Patent Application No. 200680036959.4 mailed from the State Intellectual Property Office of the People's Republic of China dated Sep. 3, 2012.
Non-final office action from U.S. Appl. No. 11/959,445 dated Sep. 10, 2013.
Restriction Requirement for U.S. Appl. No. 11/959,445 dated Feb. 3, 2014.
Decision on Rejection from the Patent Office of the State Intellectual Property Office of the People's Republic of China for Application No. 201080023548.8 dated Jan. 30, 2014.
First Office Action for Japan Patent Application No. 2012-503626 mailed from the Japan Patent Office dated Feb. 25, 2014.
Advisory Action for U.S. Appl. No. 11/959,445 dated Jun. 9, 2015.
Communication Pursuant to Article 94(3) EPC for European Patent Application No. 12158784.4 dated Feb. 16, 2017.
Communication Pursuant to Article 94(3) EPC for European Patent Application No. 12158784.4 dated May 24, 2016, 5 pages.
Decision of Dismissal of Amendment for Japanese Application No. 2012-503626 mailed from the Japan Patent Office dated Apr. 28, 2015.
Decision of Rejection for Chinese Patent Application No. 201410111418.X mailed from the State Intellectual Property Office of the People's Republic of China dated Jan. 26, 2017.
Decision of Rejection for Japanese patent Application No. 2010-539632 dated Jul. 8, 2014 from the Japan Patent Office.
Examiner Interview Summary from U.S. Appl. No. 11/959,445 dated Sep. 23, 2014.
Examiner's Report for Australian Patent Application No. 2010234785 mailed from the Australian Patent Office dated Nov. 5, 2015.
Final office action for U.S. Appl. No. 11/959,445 dated Mar. 25, 2015.
Final Office Action for Japanese Patent Application No. 2012-503626 mailed from the Japan Patent Office dated Nov. 25, 2014.
Final office action from U.S. Appl. No. 11/959,445 dated Jul. 3, 2014.
First Office Action for European Application No. 10762191.4 mailed from the European Patent Office dated May 24, 2016.
First Office Action for Japanese Patent Application No. 2010-539632 mailed by the Japan Patent Office dated Jan. 27, 2015.
First Office Action from Canadian Patent Application No. 2,709,900 mailed from the Canadian Intellectual Property Office dated Jan. 16, 2015.
Invitation Pursuant to Rule 137(4) EPC for European Patent Application No. 12158784.4 mailed from the European Patent Office dated Apr. 1, 2015.
Non-final office action for U.S. Appl. No. 11/959,445 dated Jul. 10, 2015.
Non-final office action from U.S. Appl. No. 11/959,445 dated Oct. 16, 2014.
Notice of Panel Decision from Pre-Appeal Brief Review for U.S. Appl. No. 11/959,445 dated Nov. 2, 2015.
Notice of Result of Re-Consideration Prior to Trial for Korean Patent Application No. 10-2010-7015889 mailed from the Korean Intellectual Property Office dated Apr. 7, 2016.
Notice of the First Office Action for Chinese Application No. 201410111418.X mailed from the State Intellectual Property Office of the People's Republic of China dated Dec. 16, 2015.
Notice of the Second Office Action for Chinese Patent Application No. 201410111418.X mailed from the State Intellectual Property office of the People's Republic of China dated Jun. 3, 2016.
Notice on Reexamination for Chinese Patent Application No. 201080023548.8 mailed from the State Intellectual Property Office dated Jul. 13, 2015.
Notice on Reexamination for Chinese Patent Application No. 201080023548.8 mailed from the State Intellectual Property Office dated May 8, 2015.
Office Action for Canadian Patent Application No. 2,620,780 mailed from the Canadian Intellectual Propery Office dated Sep. 2, 2016.
Office Action for Canadian Patent Application No. 2,757,285 mailed from the Canadian Intellectual Property Office dated Apr. 21, 2016.
Office Action for Canadian Patent Application No. 2757285 mailed from the Canadian Intellectual Property Office dated Jan. 16, 2017.
Office Action for Korean Patent Application No. 10-2010-7015889 mailed from the Korean Intellectual Property Office dated Oct. 30, 2015.
Office Action for Korean Patent Application No. 10-2010-7015889 mailed from the Korean Intellectual Property Office dated Apr. 14, 2015.
Office Action for Korean Patent Application No. 10-2011-7024381 mailed from the Korean Intellectual Property Office dated Apr. 21, 2016.
Office Action for Mexican Patent Application MX/a/2011/010326 mailed from the Mexican Patent Office dated Dec. 26, 2016.
Office Action from European Patent Office for European Patent Application No. 08860955.7 dated Sep. 1, 2014.
Second Office Action from Canadian Patent Application 2,620,780 mailed from the Canadian Intellectual Property Office dated Aug. 14, 2014.
Third Office Action from Canadian Patent Application 2,620,780 mailed from the Canadian Intellectual Property Office dated Jul. 9, 2015.
Notice of Allowance for U.S. Appl. No. 11/959,445 dated Aug. 2, 2016.
Communication Pursuant to Article 94(3) EPC for European Patent Application No. 08860955.7 mailed from the European Patent Office dated May 10, 2017.

\* cited by examiner

ULTRAVIOLET LIGHT TREATMENT CHAMBER

CROSS-REFERENCE TO RELATED APPLICATION(S)

This document is a continuation-in-part application that is related to, and claims priority from, U.S. patent application Ser. No. 11/959,445, also entitled "Ultraviolet Light Treatment Chamber," and filed on Dec. 18, 2007, as well as U.S. patent application Ser. No. 11/217,772, also entitled "Ultraviolet Light Treatment Chamber," and filed on Aug. 31, 2005, now U.S. Pat. No. 7,511,281 which are commonly owned, and which are hereby incorporated by this reference in their entirety.

TECHNICAL FIELD

The present invention technically relates to the treatment of fluids using ultraviolet light. More specifically, the present invention technically relates to the treatment of fluids using ultraviolet light. Even more specifically, the present invention technically relates to the treatment of fluids using ultraviolet light for deactivating microorganisms.

BACKGROUND ART

Various approaches are used to reduce contamination in liquids and gases, such as in municipal drinking water supplies, ultrapure water systems for industrial processing and pharmaceutical manufacture, water and reagents for use in experimentation, gases used in sterile rooms, and the like. Such approaches are often used to reduce or eliminate the need for chemical aerosols, chemical preservatives, microfiltration, and like materials as well as processes for the treatment of liquids and/or gases.

An apparatus for irradiating media by means of a UV light that is external to a tubular body has been described, e.g., U.S. Pat. No. 4,948,980, which is herein incorporated by reference. U.S. Pat. No. 4,948,980 provides an apparatus having a tubular body through which medium to be irradiated flows, and at least two UV light sources with reflectors arranged externally in relation to the tubular body and having parallel axes. The apparatus described in U.S. Pat. No. 4,948,980 relies on specular reflectors to control the uniformity of the light pattern delivered by the lamps. The lamp sources are relatively flat and aligned on their edges within the specular reflector in order to minimize the optical effects in the reflector. Unfortunately, U.S. Pat. No. 4,948,980 describes approaches that significantly limit the amount of dosage that can be provided to effectively treat a liquid or gas. For instance, U.S. Pat. No. 4,948,980 does not appreciate the use of a high reflectivity diffuse reflector to treat a liquid or gas with a low absorption cross-section nor does the patent anticipate a large increase in dose delivered to a target as the net reflectivity of the entire chamber approaches 100 percent.

U.S. Patent Application Publication No. 2004/0166018, herein incorporated by reference, describes a UV air sterilization chamber comprising inner surfaces having a diffuse reflective behavior. The sterilization chamber includes an inlet aperture and an outlet aperture for air to flow through the chamber and a light source emitting a UV light. Unfortunately, the approaches described in U.S. Patent Application Publication No. 2004/0166018 suffer from several problems. For example, since these approaches do not attempt to increase the transparent or translucent containment volume compared to total chamber volume, the performance of the apparatus is not maximized. In addition, the reflector used is not isolated from the medium being treated; and no option exists for replacing lamps without opening the chamber, thereby increasing the difficulty in using and maintaining the system.

In U.S. Pat. No. 6,228,332, herein incorporated by reference, discloses a short-duration, high-intensity pulsed broad-spectrum polychromatic light being used to treat water for the deactivation of microorganisms. As described in U.S. Pat. No. 6,228,332, deactivation of microorganisms in water involves illuminating the water with at least one short-duration, high-intensity pulse of broad-spectrum polychromatic light. The system includes a watertight housing having an inlet port and an outlet port for the flow water. A tubular light source for deactivating microorganisms and a tubular baffle for directing the water flow are positioned within the watertight housing. Water enters the inlet port and flows between the watertight housing and the tubular baffle in one direction, around the end of the tubular baffle and back through the center of the tubular baffle in a second direction exiting the outlet port. In this case, water flows around the tubular light source which provides at least one short-duration, high-intensity pulse of broad-spectrum polychromatic light. However, the approaches described in this patent also suffer from several problems. For example, the efficiency of the approaches described in U.S. Pat. No. 6,228,332 are limited, because these approaches do not use a reflective surface or substantially enclose the treatment chamber in order to treat the liquid or gas target.

SUMMARY OF THE INVENTION

The present invention addresses the foregoing needs and other problems in the related art. The present invention, in various embodiments, relates generally to methods and apparatuses for the treatment of liquids and gases using ultraviolet light. Approaches are described herein that advantageously allow for treating and/or reducing contamination in fluids, e.g., liquids and gases, such as in municipal drinking water supplies, ultrapure water systems for industrial processing and pharmaceutical manufacture, water and reagents for use in experimentation, gases used in sterile rooms, and the like. The present invention approaches provide easy economical implementation and provide higher effective treatment doses for the target liquid or gas for a given power input as compared with previous approaches. The approaches may be used to reduce or eliminate biological agents. Additionally, these approaches may be used to remove or eliminate or activate chemicals.

In one embodiment of the present invention, an apparatus for the treatment of a liquid includes a chamber having at least one inner surface. The chamber is at least 80 percent enclosed. The apparatus also includes an ultraviolet-(UV-) transmissive tube which is disposed within the chamber and is adapted for the passage of the liquid (or gas) therethrough. The apparatus further includes a UV lamp; and the UV lamp is disposed within the UV-transmissive tube. A reflective material is interposed between the chamber and the transmissive tube, and the reflective material is adapted so as to reflect at least a portion of light emitted by the UV lamp. In one example, the reflective material is at least 80 percent reflective. The fluid, e.g., the liquid, may, alternatively, travel between two UV-transmissive tubes, wherein one UV-transmissive tube is concentrically disposed within the other UV-transmissive tube.

In many of these embodiments, the confluence of a first light from the UV lamp and a second light (and subsequent light) reflected from the reflective material produces an unexpectedly, generally, uniform light distribution to occur within a volume of the liquid. In other words, the light distribution using the present invention approaches is generally more uniform than expected than that of related art systems.

In others of these embodiments, increased fluence is achieved due to a better reflector or reflective surface when using highly transmissive liquids or gases. In this case, a substantial of the surface area, e.g., greater than 80%, surrounding the liquid is highly reflective.

In still other embodiments, increased uniformity and increased fluence are achieved. If the transmissivity of the liquid is substantially high, the increase in uniformity may occur, but it does impact performance as much as the increased fluence.

The reflective material may be disposed in a variety of different ways. In one example, the reflective material is disposed so as to line the inner surface of the chamber. In another example, the reflective material is disposed on the outer surface of the transmissive tube. In another example, the reflective material is disposed by coating the reflective material onto the inner surface of the chamber. Yet in another example, the reflective material is disposed on the outer surface of the transmissive tube, wherein a fluid flows between the UV lamp and the transmissive tube, and wherein the UV lamp may be concentrically disposed within the transmissive tube.

The UV lamp may also be disposed in a number of different configurations and positions. In one example, the UV lamp is disposed within a transmissive protective sleeve, the transmissive protective sleeve being optionally concentrically disposed within the UV transmissive tube. Other configurations and placements of the UV lamp are possible in the present invention; e.g., off-center dispositions, by example only.

Additionally, the reflective material may be composed according to a number of different formulations. For example, the reflective material may comprise at least one material, such as polytetrafluoroethylene (PTFE), expanded polytetrafluoroethylene (ePTFE), coated aluminum, anodized aluminum, and polished aluminum. In addition, the reflective material may comprise a mixture of a binder and a reflective additive. The reflective additive may comprise at least one material, such as barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, and zirconium oxide.

The apparatus may also include an input and output port for accommodating the UV-transmissive tube, e.g., where the UV-transmissive tube enters and exits the chamber. Each of the ports may assume a number of different configurations.

Additionally, the ultraviolet irradiance provided by the present invention approaches may fall into a variety of different ranges. In one example, the ultraviolet irradiance impinging on the liquid is in the range of approximately 0.01 W/cm$^2$ to approximately 20 W/cm$^2$. Other examples of ranges are also possible and fall within the present invention.

BRIEF DESCRIPTION OF THE DRAWING

For a better understanding of the present invention, reference is made to the below-referenced accompanying Drawing(s). Reference numbers refer to the same or equivalent parts of the present invention throughout the several figures of the Drawing(s).

MODE(S) FOR CARRYING-OUT THE INVENTION

Figure 1:
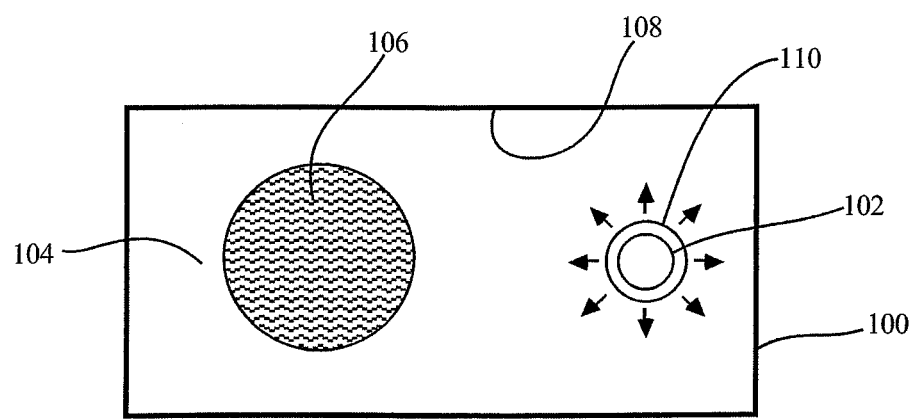
FIG. 1 is a schematic diagram of an ultraviolet light treatment system, in accordance with an embodiment of the present invention.
Figure 2:
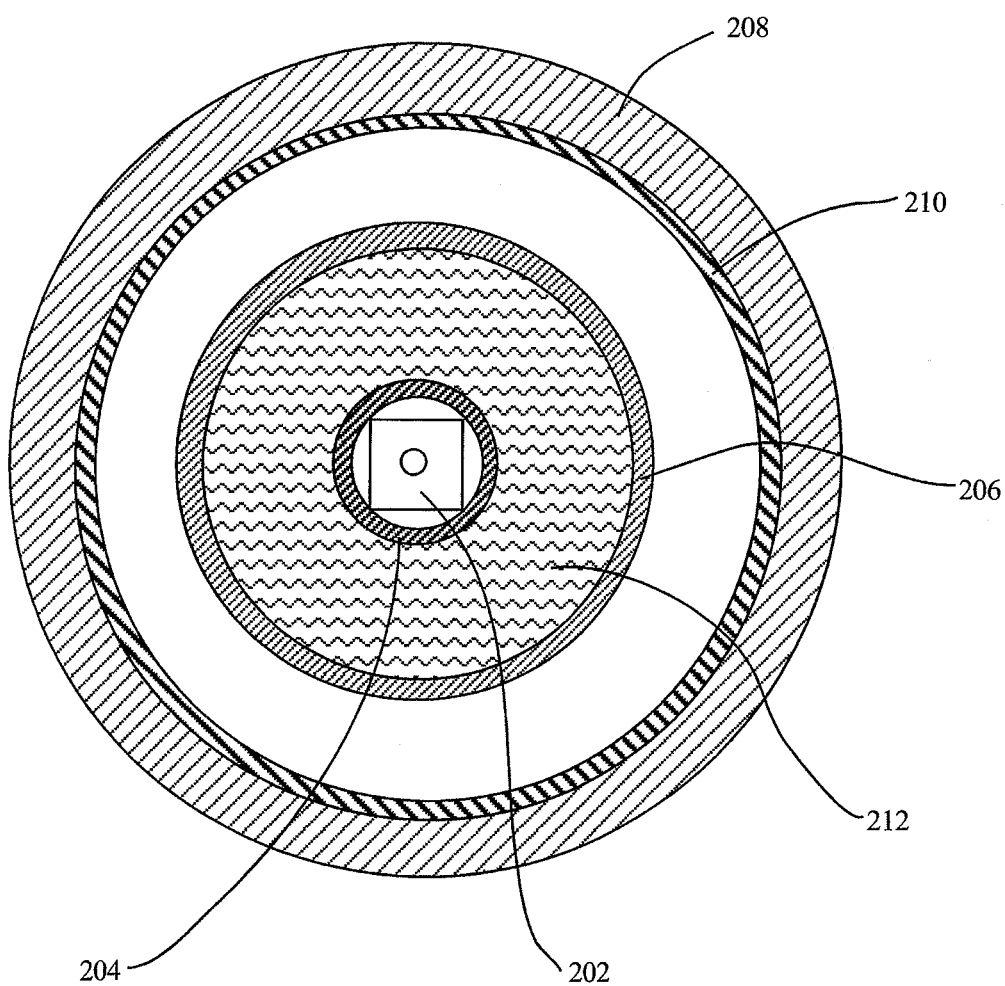
FIG. 2 is a schematic diagram of an ultraviolet treatment system, in accordance with another embodiment of the present invention.
Figure 3:
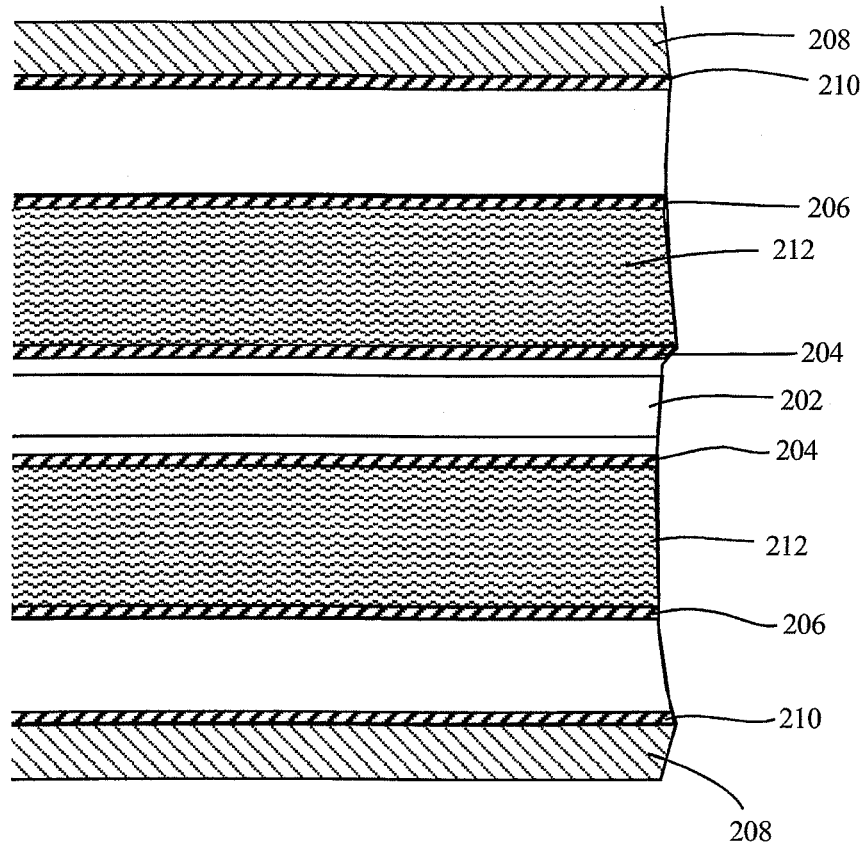
FIG. 3 is longitudinal cross-section of the ultraviolet treatment system of FIG. 2.
Figure 4:
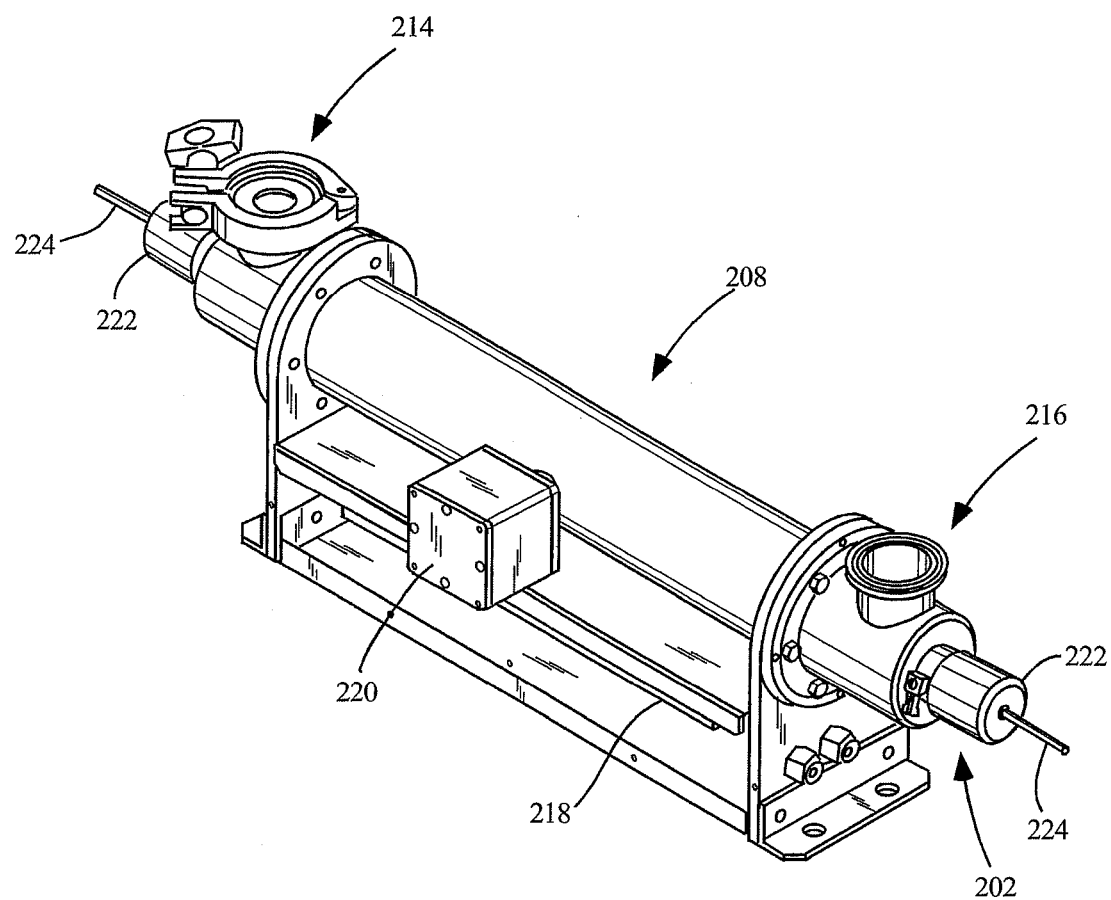
FIG. 4 is an exterior perspective view of the treatment system of FIG. 2.
Figure 5:
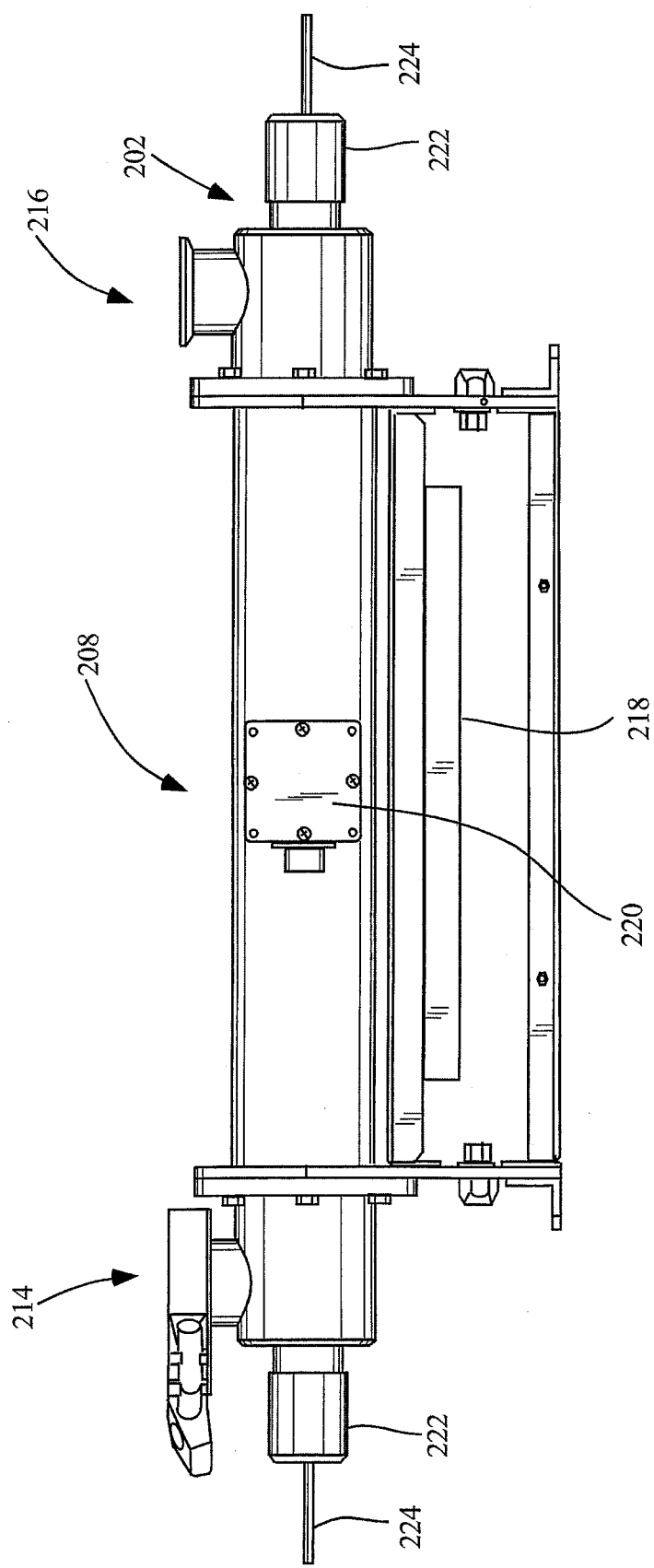
FIG. 5 is a side view of the ultraviolet treatment system of FIG. 2.

The following is a description that includes the best modes presently contemplated for practicing the invention. This description is not to be taken in a limiting sense, but is made merely for the purpose of describing the general principles of the invention and providing examples thereof. The scope of the present invention should be ascertained with reference to the issued claims.

The present apparatus provides for a large reduction in the total UV power required to treat a target liquid or gas to a specified dose level. This is accomplished by enclosing the target and the UV light source within a chamber which has walls with an extremely high-reflectivity lining or coating and by minimizing the size and number of openings in the chamber wall and absorbing surfaces within the chamber. The chamber design allows for increased photon deposition resulting in enhanced UV irradiation efficiency. Synergy is achieved by combining both of these criteria, because the dose delivered to the target increases exponentially as the chamber wall reflectivity and the percentage of the chamber enclosure approach 100 percent. The resulting synergistic effect is more efficient than the summation of the individual effect of each criteria. For example, a fully enclosed chamber, with 99%-reflective walls, will deliver 10 times the dose to the target than will an identical chamber with 90% reflective walls.

Treatment of a fluid, e.g., a liquid or a gas, within a UV-transmissive tube to separate the fluid from the chamber walls has advantages. Such a tube could be introduced into the above-described chamber. In order to maximize the dose delivered to the target within the UV-transmissive tube and the transmissive media carrying the target inside the tube, the UV-transmissive tube should enclose as much of the chamber volume as possible. This minimizes the amount of light which would otherwise be reflected between the walls without passing through the UV-transmissive tube and into the target area.

Ultraviolet light, which has shorter wavelengths than visible light, is considered to include wavelengths measuring approximately between 10 nm and approximately 400 nm, generally corresponding to frequencies between approximately $7.5 \times 10^{14}$ Hz to approximately $3 \times 10^{16}$ Hz. On the electromagnetic spectrum, ultraviolet light has wavelengths less than violet light in the visible spectrum and wavelengths greater than X-rays. Ultraviolet light is divided into three categories: near ultraviolet (NUV), which is closest to visible light, comprising wavelengths from approximately 300 nm to approximately 400 nm; far ultraviolet (FUV), located after NUV, comprising wavelengths from approximately 200 nm to approximately 300 nm; and extreme ultraviolet (EUV) located after FUV and before X-ray wavelengths, comprising wavelengths from approximately 100 nm to approximately 200 nm. Ultraviolet light is also divided, based on biological effects, into UV-A (approximately 320 nm to approximately 400 nm), UV-B (approximately 280 nm to approximately 320 nm), and UV-C (approximately 100 nm to approximately 280 nm) bands which do not directly correspond to the aforementioned designations.

While most UV irradiation processes can occur when stimulated by UV photons with wavelengths longer than 200 nm, many applications use sub-200 nm light to increase the process rates. In this regime, the efficiency of most light sources is relatively low in the related art. This low efficiency further drives the long-felt need in the related art for an efficient system to deliver the UV photons to their desired target.

Generally, the present invention methods and apparatuses for the treatment of fluids; e.g., liquids and gases, using ultraviolet light are described, infra. Although the following description is particularly directed to the treatment of fluids, understood is that the apparatus of the present embodiment may be easily adapted for the treatment of solid materials as well, such as particles in suspensions or emulsions, foodstuffs, surgical instruments, and the like. For example, the treatment chamber may be adapted to remove the tubing material and input and output ports and replaced with a cavity for the placement of a solid material. This arrangement may render the treatment chamber fully or nearly fully enclosed. Besides solid materials, fluids enclosed in a container, such as vials of reagents, pouches of blood and blood components, and other prepackaged fluids may be treated using a slightly modified apparatus of the present invention.

Ultraviolet light is useful for deactivating or killing microorganisms, including bacteria, viruses, fungi, mold spores, protozoa, and like biological materials. Deactivation is caused when ultraviolet radiation alters or mutates biomolecules, such as nucleic acids, i.e., deoxyribonucleic acid (DNA) and/or ribonucleic acid (RNA), and proteins, e.g., enzymes. When native DNA is exposed to a sufficient level of ultraviolet radiation, mutations are formed in the genetic material. The most common mutations are the 5,6-cyclobutyl dipyrimidines, pyrimidine dimers, pyrimidine adducts, pyrimidine hydrates, and DNA-protein crosslinks. Direct protein damage is less common, but indirect damage of other biomolecules resulting from proteins absorbing wavelengths greater than 290 nm, is particularly relevant. Proteins absorbent at these wavelengths generally contain tryptophan and tyrosine. In the presence of oxygen, energy transfer from the excited triplet state of tryptophan occurs, thereby producing a singlet oxygen. Thus, tryptophan in protein acts as an endogenous photosensitizer in the UVB wavelength range by producing free-radical oxygen which reacts with proteins, unsaturated lipids, and bases in nucleic acids. In any case, ultraviolet radiation promotes the generation of singlet oxygen and hydroxyl-free radicals which can damage cellular proteins, lipids, and carbohydrates.

Membranous microorganisms are deactivated or killed when ultraviolet radiation penetrates the organism's membrane and alters its genetic material and, to a lesser extent, proteins, e.g., enzymes. In cases where an organism has sustained significant biomolecular damage, the microorganism may die. In cases where the genetic and/or proteinaceous material has been altered, but perhaps not completely destroyed, the microorganism may no longer be able to reproduce. Without the ability to reproduce, coupled with the short lifespan of most microorganisms, population size will diminish rapidly in material treated with ultraviolet radiation.

In the case of viruses, ultraviolet radiation mutates the genetic material such that the viruses are no longer capable of infecting host cells and/or multiplying within a host organism using the host's cellular machinery. The UV dose for deactivating 99.99% of typical bacteria, such as *Enterobacteria cloacae, Klebsiella pneumoniae, Pseudomonas aeruginosa, Salmonella typhimurium* A, *Vibrio cholerae*, and *Escherichia coli*, in a range of approximately 20 mJ/cm$^2$ to 30 mJ/cm$^2$. For spore forming bacteria such as *Bacillus subtilis* in the sporulated state, the dose is higher, e.g., usually at least approximately 60 mJ/cm$^2$. Deactivation of viruses, such as polio and rotavirus, requires a dose in a range of approximately 30 mJ/cm$^2$ to approximately 40 mJ/cm$^2$, but other viruses can require higher doses. Protozoa, such as *Cryptosporidium parvum* and *Giardia muris*, have been killed with doses as low as approximately 10 mJ/cm$^2$ (Ultraviolet Applications Handbook, 2$^{nd}$ Ed., James R. Bolton, Bolton Photosciences, Inc., 2001, p. 37).

Ultraviolet light is also used to decompose chemicals, particularly organic chemicals, into components which are safer or which can be more easily removed by activated carbon filtration, resin beds, or reverse osmosis, any of which are features which may be used in conjunction with the present apparatus and methods. This decomposition results from both direct photon absorption or by decomposition by OH— radicals which are produced in the proximity of the chemical molecule by the interaction of the ultraviolet light with water molecules or possibly other sources of OH— radicals. The decomposition may be also be achieved by using advanced oxidation methods, such as adding ozone or hydrogen peroxide in combination with using ultraviolet light.

A table of dissociation wavelengths and the maximum wavelength which can cause this dissociation for common chemical bonds in organic substances follows: The application of UV technology to pharmaceutical water treatment," Bakthisaran, S., European_Journal of Parenteral Sciences, 3(4), pp. 97-102, 1998.

| Dissociation Energies for Interatomic Bonds in Organic Substances | | |
|---|---|---|
| Chemical Bond | Dissociation Energy (UV Dose) (kcal/gmol) | Maximum Wavelength for Dissociation (nm) |
| C—C | 82.6 | 346.1 |
| C=C | 14.5 | 196.1 |
| C≡C | 199.6 | 143.2 |
| C—Cl | 81.0 | 353.0 |
| C—F | 116.0 | 246.5 |
| C—H | 98.7 | 289.7 |
| C—N | 72.8 | 392.7 |
| C=N | 147.0 | 194.5 |
| C≡N | 212.6 | 134.5 |
| C—O | 85.5 | 334.4 |

-continued

Dissociation Energies for Interatomic Bonds in Organic Substances

| Chemical Bond | Dissociation Energy (UV Dose) (kcal/gmol) | Maximum Wavelength for Dissociation (nm) |
|---|---|---|
| C=O (aldehydes) | 176.0 | 162.4 |
| C=O (ketones) | 179.0 | 159.7 |
| C—S | 65.0 | 439.9 |
| C=S | 166.0 | 172.2 |
| H—H | 104.2 | 274.4 |
| N—N | 52.0 | 549.8 |
| N=N | 60.0 | 476.5 |
| N≡N | 226.0 | 126.6 |
| N—H (NH) | 85.0 | 336.4 |
| N—H (NH3) | 102.2 | 280.3 |
| N—O | 48.0 | 595.6 |
| N=O | 162.0 | 176.5 |
| O—O ($O_2$) | 119.1 | 240.1 |
| —O—O— | 47.0 | 608.3 |
| O—H (water) | 117.5 | 243.3 |
| S—H | 83.0 | 344.5 |
| S—N | 115.2 | 248.6 |
| S—O | 119.0 | 240.3 |

Turning to FIG. 1, a schematic diagram of a treatment chamber is depicted, in accordance with the present invention. Shown are a chamber 100, an ultraviolet lamp 102, an ultraviolet transmissive tube 104, a fluid, e.g., a liquid, 106, a light reflective material 108, and an optional UV-transmissive tube (or lamp sleeve) 110. Alternatively, the ultraviolet lamp may be enclosed within the ultraviolet transmissive tube 104. The chamber 100 contains an ultraviolet lamp 102 and an ultraviolet transmissive tube 104. The ultraviolet lamp 102 may be enclosed by the optional transmissive tube 110. The chamber 100 may be coated or covered or lined with a light reflective material 108, as shown in FIG. 1. The ultraviolet lamp 102 may be located in a physically separate position, as shown in FIG. 1, from the ultraviolet transmissive tube 104. The light transmissive tube 104 runs through the chamber 100 where it is exposed to ultraviolet light provided by the ultraviolet lamp 102. The tube 104 may carry any type of fluid, e.g., a liquid 106 or a gas, including for example, water, air, experimental reagents, blood components, e.g., red blood cells, white blood cells, and plasma, beverages for consumption, and the like. Therefore, as the liquid 106 passes through the ultraviolet transmissive tube 104, the liquid 106 is exposed to ultraviolet photons useful for the treatment of the liquid 106.

The chamber 100 of FIG. 1 has an input and output port (not shown) for an ultraviolet transmissive tube 104 to run through chamber 100. However, the input and output ports are fashioned as such to render the chamber 100 as substantially enclosed as possible. For example, the input and/or output ports may utilize elbow, coiled, or other serpentine paths for gas and/or liquid flow to increase enclosure of the chamber 100. To further enhance enclosure, the flow path may be constricted to a smaller diameter and/or the reflector may be extended to a distance beyond the zone in which light is introduced. Additionally, certain features such as baffles may also be incorporated into the apparatus to optimize light containment within the chamber 100. In any case, any number and combination of the aforementioned techniques and devices may be used to increase chamber enclosure. As is further described herein below, the apparatus reaches maximum efficiency when the chamber 100 approaches 100 percent enclosure and the reflective material 108 approaches 100 percent reflectivity.

Although the chamber 100, depicted in FIG. 1, is coated with a reflective material 108, understood is that any type of reflective material 108 or apparatus may be used. For example, the reflective material 108 which may be coated on the inside of the chamber 100 may comprise at least one material, such as polytetrafluoroethylene (PTFE), expanded polytetrafluoroethylene (ePTFE), and other similar plastic. The reflective material 108 may be coated, anodized, or polished aluminum. In another embodiment, the reflective material 108 may be a reflector such as a diffuse or specular reflector, near, but not necessarily attached, to the chamber wall. Any type of specular reflector, in any type of shape, may be used with the present embodiment. In any form, the reflective material 108 should have a high level of reflectivity. In one embodiment, the reflectivity level of the reflective material 108 is in the range of 80 percent to 100 percent, and more preferably, 90 percent to 100 percent.

Although the exact percent reflectivity may change depending on the particular needs of an apparatus, understood is that the higher the reflectivity, the higher the efficiency of the treatment chamber. For example, a fully enclosed chamber comprising a material with a 90 percent reflectivity will have a lower dose on the target in comparison to a fully enclosed chamber comprising a reflective material with a 99 percent reflectivity. Assuming that the exemplary target and walls are the only absorbers in the chamber, on average a photon will be reflected back and forth 10 times more in the 99 percent reflective chamber than the 90 percent reflective chamber before being absorbed by the reflective material. Thus, the photons are 10 times more likely to be absorbed by the target in a 99 percent reflective chamber than the 90 percent reflective chamber when the chamber is entirely enclosed. Therefore, the 99 percent reflective chamber delivers 10 times the ultraviolet light dose on the target as the 90 percent reflective chamber.

Similarly, a 99 percent enclosed chamber will deliver a higher ultraviolet light dose on a target than a 90 percent enclosed chamber. In a less enclosed chamber, photons are more likely to be reflected out of the chamber, thus reducing the likelihood of the photons being absorbed by the target. As such, the dosage of ultraviolet light treatment ultimately delivered to a target material is inversely related to absorbance where reflectivity of the apparatus components and enclosability of the chamber affects absorbance.

The ultraviolet lamp 102 may be of any type useful for providing ultraviolet radiation, such as low pressure mercury lamps, medium pressure mercury lamps, excimer lamps, flashlamps with xenon and other fill mixtures, and microwave-driven lamps. The ultraviolet lamp provides at least one wavelength less than approximately 400 nm to a target for the deactivation or killing of biological materials, the direct destruction of chemicals, and the indirect destruction of chemicals through advanced oxidation by therein using oxidizing agents, such as $H_2O_2$ and $O_3$. The ultraviolet lamp 102 may be enclosed by the optional transmissive tube 110 thereby allowing a technician to safely change the lamp 102 without opening the main chamber. Such a tube 110 is optional and may be applied to the present embodiment for ease of operation; however, the present embodiment will function without the tube 110.

The ultraviolet transmissive tube 104 comprises any material that is substantially transmissive to ultraviolet light. To achieve maximum efficiency of the treatment chamber, an ultraviolet transmissive tube material, having near 100 percent transmissivity as possible, is preferred. In cases where 100 percent transmissivity is not possible, materials such as fused silica (Heraeus Heralux, Momentive 214), synthetic quartz (Heraeus Suprasil, Momentive 021 and 022), fluorine doped silica (Asahi Glass AQX), and sapphire (Saphikon EFG sapphire), being generally higher than 80 percent transmissive in the wavelengths below 300 nm, are useful.

Other examples of configurations for systems of treating liquids are shown in co-pending U.S. patent application Ser. No. 11/217,772 entitled "ULTRAVIOLET LIGHT TREATMENT CHAMBER" and which has been herein incorporated by reference in its entirety.

Referring now to FIGS. 2-5, another example of a system for the ultraviolet (UV) treatment of liquids or gases is described. The system includes a lamp 202, which is encased within an inner sleeve 204. The inner sleeve 204 is itself enclosed in a transmissive tube 206 (or a protective layer); and the transmissive tube 206 is disposed within a treatment chamber 208. The treatment chamber 208 has a reflective material 210 interposed between the transmissive tube 206 and the treatment chamber 208. In this example, the reflective material 210 is disposed on its inner surface forming a reflective surface. In a variation, reflective material 210 may be disposed on the outer surface of the transmissive tube 206 forming a reflective surface. Alternatively, the reflective material 210 may be attached to the transmissive tube 206 forming a reflective surface or the reflective material 210 may be a freestanding structure having a reflective surface. Other placements and configurations for the reflective material 210 are possible forming a reflective surface enveloping by, for example, eighty percent, the lamp 202. A liquid or gas 212 passes through the transmissive tube 206. In one example, the treatment chamber 208 is at least 80 percent enclosed.

The transmissive tube 206 runs through the chamber 208 where it is exposed to ultraviolet light provided by the ultraviolet lamp 202. The tube 206 may carry any type of liquid or gas 212, including for example, water, air, experimental reagents, blood components, e.g., red blood cells, white blood cells, plasma, beverages for consumption, and the like. Therefore, as the liquid or gas 212 passes through the ultraviolet transmissive tube 206, the liquid 212 (or gas) is exposed to ultraviolet photons useful for treating the liquid or gas 212 (and/or items within the liquid or gas 212). A UV monitor 220 monitors the level of UV radiation in the treatment chamber 208.

The treatment chamber 208 has an input port 214 and an output port 216 that allow for the ultraviolet transmissive tube 206 to run through the chamber 208. In other examples, the roles of the input port 214 and output port 216 are reversed. The input port 214 and the output port 216 are fashioned as such to render the chamber 208 as substantially enclosed as possible. For example, the input port 214 and/or output port 216 may utilize elbow, coiled, or other serpentine paths for gas and/or liquid flow to increase enclosure of the chamber 208. To further enhance enclosure, the flow path may be constricted to a smaller diameter and/or the reflective material 210 may be extended to a distance beyond the zone in which light is introduced. Additionally, additional structures such as baffles may also be incorporated into the apparatus to optimize chamber concealment. In any case, any number and combination of the aforementioned techniques, structures, and devices may be used to increase chamber enclosure.

Although the chamber 208 depicted in FIGS. 2-5 is coated with a reflective material 210, understood is that any type of reflective material 210 or reflective structure may be used. For example, the reflective material 210 which may be coated or lined on the inside of the chamber 208 may comprise at least one material, such as polytetrafluoroethylene (PTFE), expanded polytetrafluoroethylene (ePTFE), or other similar plastics, and may be coated, anodized, or polished aluminum. In another example, the reflective material 210 may be a reflector such as a diffuse or specular reflector. Any type of specular reflector, in any type of shape, may be used with the present example. In many examples, the reflective material 210 has a high level of reflectivity. For instance, the reflectivity level of the reflective material 210 may be in the range of 80 percent to 100 percent, and some approaches are 90 percent to 100 percent.

Although the exact percent reflectivity of the reflective material 210 may change depending on the particular needs of an apparatus, it should be understood that the higher the reflectivity, the higher the efficiency of the treatment chamber 208. For example, a fully enclosed chamber comprising a material with a 90 percent reflectivity in comparison to a fully enclosed chamber comprising a reflective material with a 99 percent reflectivity will have a lower dose on the target. Assuming that the exemplary target and walls are the only absorbers in the chamber, on average a photon will be reflected back and forth 10 times more in the 99 percent reflective chamber than the 90 percent reflective chamber before being absorbed by the reflective material. Thus, the photons are 10 times more likely to be absorbed by the target in a 99 percent reflective chamber than the 90 percent reflective chamber when the chamber is entirely enclosed. Therefore, the 99 percent reflective chamber delivers 10 times the ultraviolet light dose on the target as the 90 percent reflective chamber.

Similarly, a 99 percent enclosed chamber will deliver a higher ultraviolet light dose on a target than a 90 percent enclosed chamber. In a less enclosed chamber, photons are more likely to be reflected out of the chamber, thus reducing the likelihood of the photons being absorbed by the target. As such, the dosage of ultraviolet light treatment ultimately delivered to a target material is inversely related to absorbance where reflectivity of the apparatus components and enclosability of the chamber affects absorbance.

The ultraviolet lamp 202 may be of any type useful for providing ultraviolet radiation. For example, low pressure mercury lamps, medium pressure mercury lamps, excimer lamps, flashlamps with xenon and other fill mixtures, and microwave-driven lamps may be used. Other examples of lamps are possible. In one example, the ultraviolet lamp 202 provides at least one wavelength less than 400 nm to a target for the deactivation or killing of biological materials therein. In another example, the ultraviolet lamp 202 provides at least one wavelength less than 400 nm to a target for the destruction of chemical compounds. The ultraviolet lamp 202 is connected to a power cable 224 in order to receive power. Additionally, end caps 22 may cover the ends of the lamp 202 to provide protection for the lamp 202. Furthermore, a lamp ballast 208 is also provided to, for example, limit current for the lamp 202.

Furthermore, an additional structure or layer exterior to the reflective material 210 may be provided to protect the reflective material 210, contain pressure, or both. Additionally, the transmissive tube 206 (or a protective layer) may contain system pressure.

As mentioned, the ultraviolet lamp 202 is enclosed by the inner sleeve 204, which allows a technician to change out the lamp 202 without opening the chamber 208. The inner sleeve 204 and the ultraviolet transmissive tube 206 may be of any material that is substantially transmissive to ultraviolet light. To achieve maximum efficiency of the treatment chamber 208, in some approaches, the material used for the inner sleeve 204 and the transmissive tube 206 is near 100 percent transmissivity as possible. In cases where 100 percent transmissivity is not possible, materials, such as fused silica (Heraeus Heralux, Momentive 214), synthetic quartz (Heraeus Suprasil, Momentive 021 and 022), fluorine doped silica (Asahi Glass AQX), and sapphire (Saphikon EFG sapphire), being generally higher than 80 percent transmissive in the wavelengths below 300 nm, are useful.

Due to the high reflectivity of the reflective material 210 in the present example, the vast majority of the ultraviolet photons are deposited into the liquid or gas (and/or to items within the liquid or gas 212) instead of the walls of the chamber 208. Consequently, the liquid or gas 212 (and/or items in the liquid or gas 212) receive a higher effective dose of radiation for a given input power.

Due to the lack of losses in other parts of the system, the upper limit to the number of photons that are absorbed by the liquid or gas 212 (and/or items within the liquid or gas 212) is multiplied by a factor roughly equal to the ratio of losses of the wall material of the chamber 208, e.g., as low as 1 percent, to that of stainless steel, e.g., 40 percent. The exact increase in UV dosage is affected by a variety of factors such as the number and size of penetrations into the volume containing the ultraviolet lamp 202 and liquid or gas 212, and any other disruptions in the surface of the reflective material 210. The overall increase in dosage over previous semi-reflective chambers, e.g., stainless steel chambers, is significant.

As mentioned, increased fluence may also be achieved due to a better reflector or reflective surface when using highly transmissive liquids. In this case, a substantial of the surface area, e.g., greater than 80%, surrounding the liquid is highly reflective.

In still other examples, increased uniformity and increased fluence are achieved. If the transmissivity of the liquid is substantially high, the increase in uniformity may occur but does impact performance as much as the increased fluence.

The increased dosage described above is accompanied by an unexpected increase in uniformity of the dose throughout the chamber, when compared to a system with a semi-reflective chamber wall. Normally, with higher fluence, a decrease in uniformity is expected, but the effect of minimizing the photon losses other than within the target gas or liquid produces a more uniform deposition of those photons within the target. This effect is essentially independent of geometry and primarily depends on the total reflectivity of the chamber walls or enclosure and on the transmissivity of the components involved.

A separate uniformity-enhancing effect which occurs for a different reason than the one above arises under certain conditions in this chamber. This effect is dependent upon the geometry of the chamber. It is also important only over a range of transmissivities of the liquid or gas 212. If the transmissivity of the liquid or gas 212 exceeds 90-95% (attenuation of 5-10%) over the distance from the light source to the chamber wall, then the effect described above does much more to create an unexpected uniformity of fluence in the chamber, and the effect described below is negligible. If the transmissivity is less than 5-10% (attenuation of 90-95%) over the distance from the light source to the chamber wall, then a very small amount of light reaches the chamber wall and once again the effect described below is negligible. For the range of transmissivities in the liquid or gas 212 such that the attenuation falls between nominally 5% and 95%, the effect described below is important in providing more uniform fluence to the target.

Further, the ultraviolet irradiance provided by the present approaches may fall into a variety of different ranges. In one example, the ultraviolet irradiance impinging on the liquid is in a range of approximately 0.01 W/cm² to approximately 20 W/cm². Other examples of ranges are possible.

Figure 6:
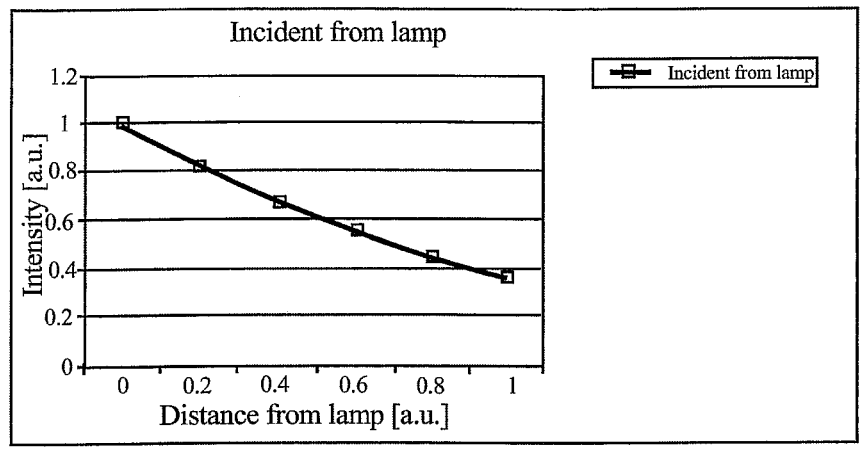
FIGS. 6-8 are charts showing light absorption properties of an ultraviolet light treatment system in accordance with various embodiments of the present invention.
Figure 7:
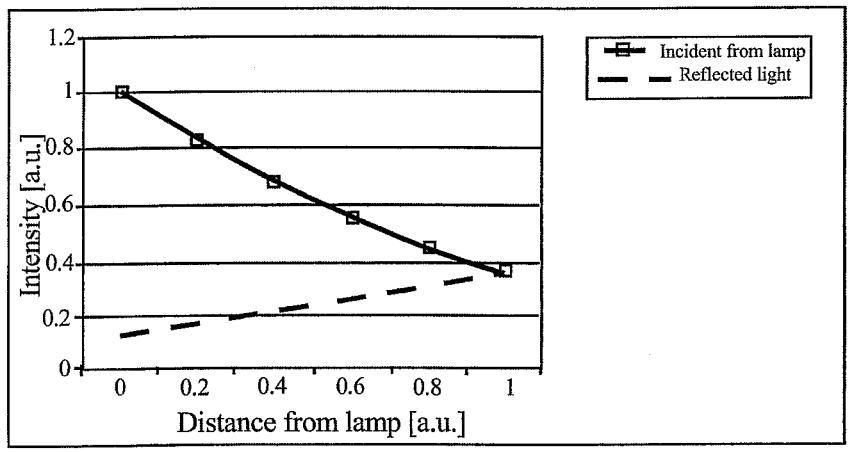
Figure 8:
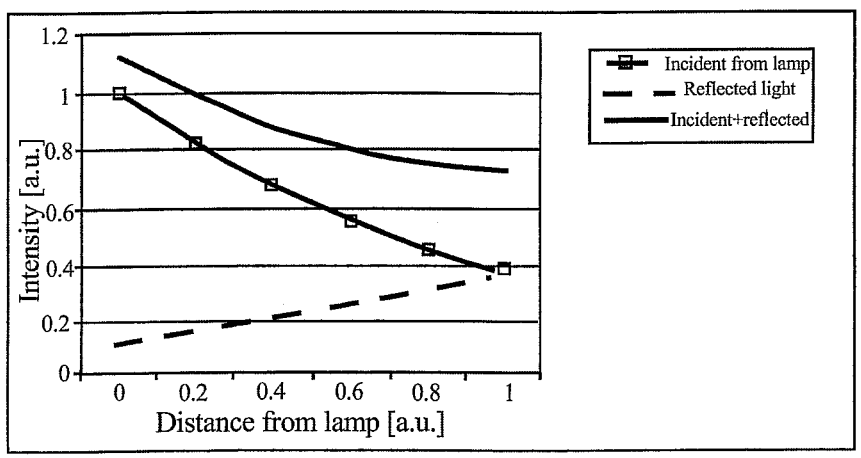

Referring now to FIGS. 6-8, the light absorption properties of the some present are herein described. The intensity of light which is transmitted through an absorbing medium is governed by Beer's Law:

$$I = I_o e^{-\alpha x}$$

where $I_o$ is the initial intensity, x is the distance traveled through the absorbing medium, e is the base of natural logarithms (e=2.718282), and α is an attenuation constant determined by the characteristics of the medium. If the medium and its dimensions are such that only a significant fraction of the light is absorbed after a single pass through the medium, then the effect shown in FIGS. 6-8 occurs.

FIG. 6 plots the intensity of light that enters the medium (Distance=0) to a particular distance x into the medium (Distance=1, with arbitrary units) at which the intensity is 1/e, e.g., approximately ⅓, of the incident intensity. If there is a non-reflecting surface at x, then the remaining light is absorbed and the difference in intensity (and therefore, the dose) between Distance=0 and Distance=wherein x=0.72.

FIG. 7 shows the same situation, but with a 100% reflector replacing the non-reflective surface at Distance=x. The reflected light is attenuated at the same rate as the incident light as it travels back through the medium. The intensity of light at a given distance is approximately the sum of the incident and the reflected light. For simplicity, any reflected light from the surface at Distance=0 is neglected. In many applications, that light would be reabsorbed or transmitted away, so neglecting it is a good approximation in many circumstances.

The intensity due to the sum of these two curves is shown in FIG. 8. In this case, the peak intensity is higher (1.14 vs. 1.00); and, in addition, the difference in intensity between Distance=0 and Distance=x is 1.54. This example shows that the intensity is much more uniform throughout the medium due to the presence of the reflective material. The improvement in uniformity of intensity; therefore, the dose is more than 70% in this example. The improvement in uniformity in intensity results in higher treatment efficiency and a lower peak intensity (less overdosing) to achieve a given dose in the media, both of which are significant improvements over prior reflectorless systems. In other words, FIG. 8 shows the generally uniform light distribution properties of the present approaches described herein.

Figure 9:
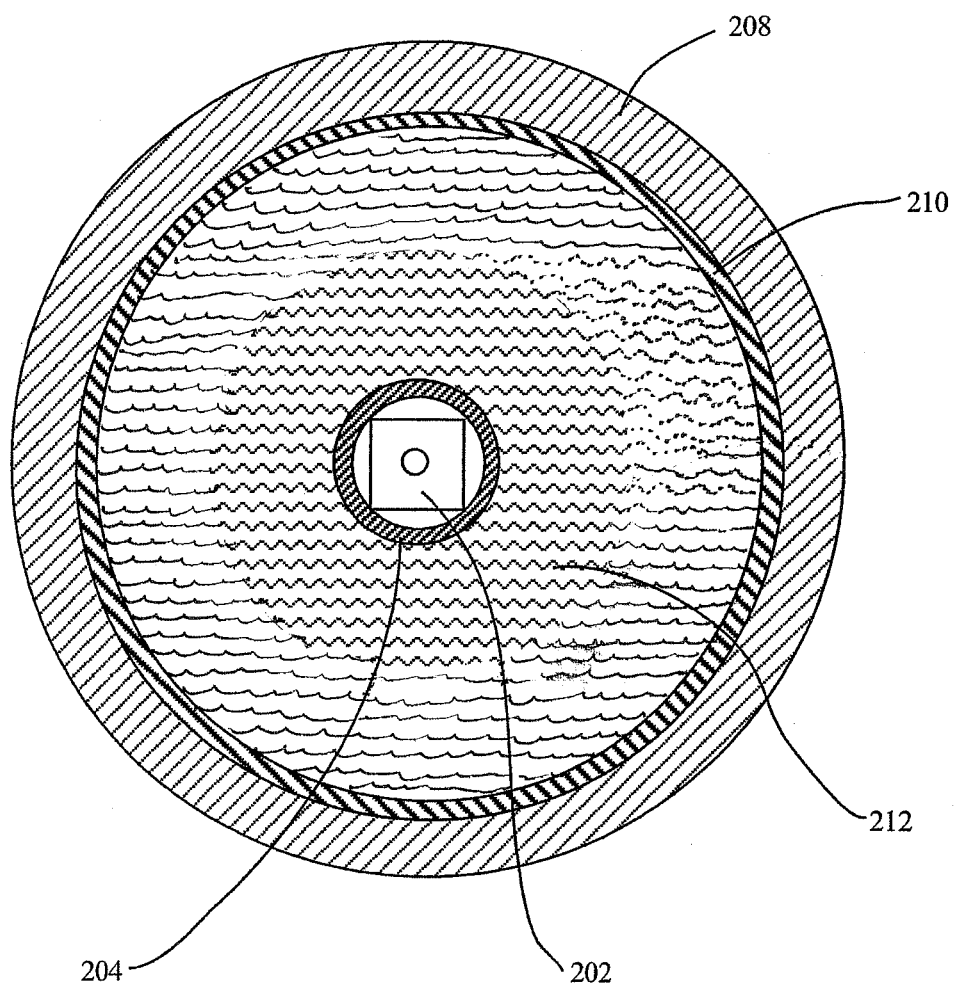
FIG. 9 is the schematic diagram, showing a treatment system having the reflective material disposed on an inner surface of a chamber, in accordance with an alternative embodiment of the present invention.

FIG. 9 illustrates, in a schematic diagram, showing a treatment system having a reflective material 210 disposed on an inner surface of a chamber 208, in accordance with an alternative embodiment of the present invention. In FIG. 9 and referring back to like elements shown in FIGS. 2-5, another example of a system for the ultraviolet (UV) treatment of liquids or gases is described. The system includes a lamp 202, which is encased within an inner sleeve 204. The inner sleeve 204 is itself enclosed in a transmissive tube 206 (or a protective layer); and the transmissive tube 206 is disposed within the treatment chamber 208 having a reflective material 210 interposed between the inner sleeve 204 and the treatment chamber 208. In this example, the reflective material 210 is disposed on an inner surface of the chamber 208 forming a reflective surface. A fluid, e.g., a liquid or gas 212, passes through the treatment chamber 208. In one example, the treatment chamber 208 is at least 80 percent enclosed.

The chamber 208 may carry any type of liquid or gas 212, including for example, water, air, experimental reagents, blood components, e.g., red blood cells, white blood cells, plasma, beverages for consumption, and the like. Therefore, as the liquid or gas 212 passes through the chamber 208, the liquid 212 (or gas) is exposed to ultraviolet photons useful for treating the liquid or gas 212 (and/or items within the liquid or gas 212). A UV monitor 220 monitors the level of UV radiation in the treatment chamber 208.

The treatment chamber 208 has an input port 214 and an output port 216 that allow for the liquid or gas 212 to flow through the chamber 208. In other examples, the roles of the input port 214 and output port 216 are reversed. The input port 214 and the output port 216 are fashioned as such to render the chamber 208 as substantially enclosed as possible. For example, the input port 214 and/or output port 216 may utilize elbow, coiled, or other serpentine paths for gas and/or liquid flow to increase enclosure of the chamber 208. To further enhance enclosure, the flow path may be constricted to a smaller diameter and/or the reflective material 210 may be extended to a distance beyond the zone in which light is introduced. Additionally, additional structures such as baffles may also be incorporated into the apparatus to optimize chamber concealment. In any case, any number and combination of the aforementioned techniques, structures, and devices may be used to increase chamber enclosure.

Although the chamber 208, depicted in FIG. 9 and FIGS. 2-5, is coated with a reflective material 210, understood is that any type of reflective material 210 or reflective structure may be used. For example, the reflective material 210 which may be coated or lined on the inside of the chamber 208 may comprise at least one material, such as polytetrafluoroethylene (PTFE), expanded polytetrafluoroethylene (ePTFE), or other similar plastics, and may be coated, anodized, or polished aluminum. In another example, the reflective material 210 may be a reflector such as a diffuse or specular reflector. Any type of specular reflector, in any type of shape, may be used with the present example. In many examples, the reflective material 210 has a high level of reflectivity. For instance, the reflectivity level of the reflective material 210 may be in the range of 80 percent to 100 percent, and some approaches are 90 percent to 100 percent.

Although the exact percent reflectivity of the reflective material 210 may change depending on the particular needs of an apparatus, understood is that the higher the reflectivity, the higher the efficiency of the treatment chamber 208. For example, a fully enclosed chamber comprising a material with a 90 percent reflectivity in comparison to a fully enclosed chamber comprising a reflective material with a 99 percent reflectivity will have a lower dose on the target. Assuming that the exemplary target and walls are the only absorbers in the chamber, on average a photon will be reflected back and forth 10 times more in the 99 percent reflective chamber than the 90 percent reflective chamber before being absorbed by the reflective material. Thus, the photons are 10 times more likely to be absorbed by the target in a 99 percent reflective chamber than the 90 percent reflective chamber when the chamber is entirely enclosed. Therefore, the 99 percent reflective chamber delivers 10 times the ultraviolet light dose on the target as the 90 percent reflective chamber.

Similarly, a 99 percent enclosed chamber will deliver a higher ultraviolet light dose on a target than a 90 percent enclosed chamber. In a less enclosed chamber, photons are more likely to be reflected out of the chamber, thus reducing the likelihood of the photons being absorbed by the target. As such, the dosage of ultraviolet light treatment ultimately delivered to a target material is inversely related to absorbance where reflectivity of the apparatus components and enclosability of the chamber affects absorbance.

The ultraviolet lamp 202 may be of any type useful for providing ultraviolet radiation. For example, low pressure mercury lamps, medium pressure mercury lamps, excimer lamps, flashlamps with xenon and other fill mixtures, and microwave-driven lamps may be used. Other examples of lamps are possible. In one example, the ultraviolet lamp 202 provides at least one wavelength less than 400 nm to a target for the deactivation or killing of biological materials therein. In another example, the ultraviolet lamp 202 provides at least one wavelength less than 400 nm to a target for the destruction of chemical compounds. The ultraviolet lamp 202 is connected to a power cable 224 in order to receive power. Additionally, end caps 22 may cover the ends of the lamp 202 to provide protection for the lamp 202. Furthermore, a lamp ballast 208 is also provided to, for example, limit current for the lamp 202.

Furthermore, an additional structure or layer exterior to the reflective material 210 may be provided to protect the reflective material 210, contain pressure, or both. Additionally, the transmissive tube 206 (or a protective layer) may contain system pressure.

As mentioned, the ultraviolet lamp 202 is enclosed by the inner sleeve 204, which allows a technician to change out the lamp 202 without opening the chamber 208. The inner sleeve 204 may be of any material that is substantially transmissive to ultraviolet light. To achieve maximum efficiency of the treatment chamber 208, in some approaches, the material used for the inner sleeve 204 is near 100 percent transmissivity as possible. In cases where 100 percent transmissivity is not possible, materials, such as fused silica (Heraeus Heralux, Momentive 214), synthetic quartz (Heraeus Suprasil, Momentive 021 and 022), fluorine doped silica (Asahi Glass AQX), and sapphire (Saphikon EFG sapphire), being generally higher than 80 percent transmissive in the wavelengths below 300 nm, are useful.

Due to the high reflectivity of the reflective material 210 in the present example, the vast majority of the ultraviolet photons are deposited into the liquid or gas (and/or to items within the liquid or gas 212) instead of the walls of the chamber 208. Consequently, the liquid or gas 212 (and/or items in the liquid or gas 212) receive a higher effective dose of radiation for a given input power.

Due to the lack of losses in other parts of the system, the upper limit to the number of photons that are absorbed by the liquid or gas 212 (and/or items within the liquid or gas 212) is multiplied by a factor roughly equal to the ratio of losses of the wall material of the chamber 208, e.g., as low as 1 percent, to that of stainless steel, e.g., 40 percent. The exact increase in UV dosage is affected by a variety of factors such as the number and size of penetrations into the volume containing the ultraviolet lamp 202 and liquid or gas 212, and any other disruptions in the surface of the reflective material 210. The overall increase in dosage over previous semi-reflective chambers, e.g., stainless steel chambers, is significant.

As mentioned, increased fluence may also be achieved due to a better reflector or reflective surface when using highly transmissive liquids. In this case, a substantial of the surface area, e.g., greater than 80%, surrounding the liquid is highly reflective.

In still other examples, increased uniformity and increased fluence are achieved. If the transmissivity of the liquid is substantially high, the increase in uniformity may occur but does impact performance as much as the increased fluence.

The increased dosage described above is accompanied by an unexpected increase in uniformity of the dose throughout the chamber, when compared to a system with a semi-reflective chamber wall. Normally, with higher fluence, a decrease in uniformity is expected, but the effect of minimizing the photon losses other than within the target gas or liquid produces a more uniform deposition of those photons within the target. This effect is essentially independent of geometry and primarily depends on the total reflectivity of the chamber walls or enclosure and on the transmissivity of the components involved.

A separate uniformity-enhancing effect which occurs for a different reason than the one above arises under certain conditions in this chamber. This effect is dependent upon the geometry of the chamber. It is also important only over a range of transmissivities of the liquid or gas 212. If the transmissivity of the liquid or gas 212 exceeds 90-95% (attenuation of 5-10%) over the distance from the light source to the chamber wall, then the effect described above does much more to create an unexpected uniformity of fluence in the chamber, and the effect described below is negligible. If the transmissivity is less than 5-10% (attenuation of 90-95%) over the distance from the light source to the chamber wall, then a very small amount of light reaches the chamber wall and once again the effect described below is negligible. For the range of transmissivities in the liquid or gas 212 such that the attenuation falls between nominally 5% and 95%, the effect described below is important in providing more uniform fluence to the target.

Further, the ultraviolet irradiance provided by the present approaches may fall into a variety of different ranges. In one example, the ultraviolet irradiance impinging on the liquid is in a range of approximately 0.01 W/cm² to approximately 20 W/cm². Other examples of ranges are possible.

Referring back to FIGS. 6-8 in relation to FIG. 9, the light absorption properties of the some present are herein described. The intensity of light which is transmitted through an absorbing medium is governed by Beer's Law:

$$I = I_o e^{-\alpha x}$$

where $I_o$ is the initial intensity, x is the distance traveled through the absorbing medium, e is the base of natural logarithms (e=2.718282), and α is an attenuation constant determined by the characteristics of the medium. If the medium and its dimensions are such that only a significant fraction of the light is absorbed after a single pass through the medium, then the effect shown in FIGS. 6-8 occurs.

Figure 10:
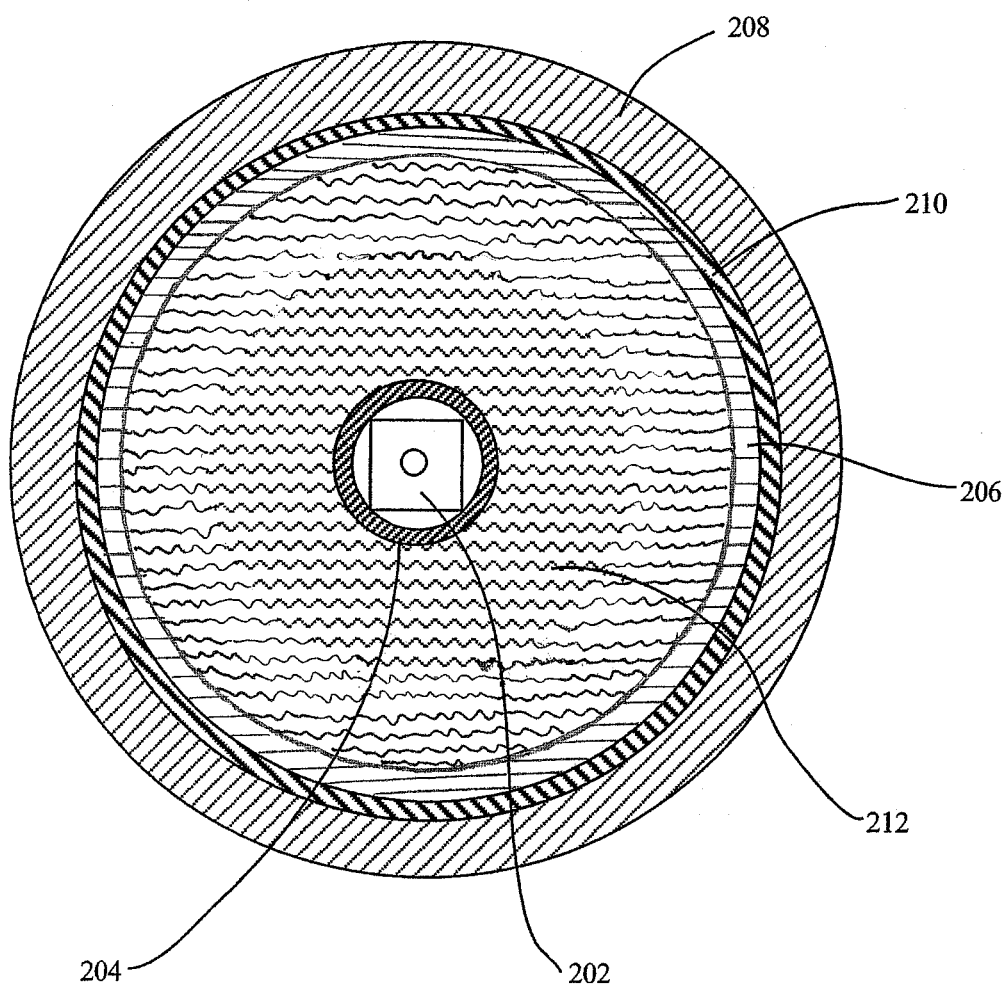
FIG. 10 is a schematic diagram, showing the fluid being disposed between two UV-transmissive tubes in accordance with an alternative embodiment of the present invention.

FIG. 10 illustrates, in a schematic diagram, showing a treatment system having a reflective material 210 disposed on an outer surface of a UV-transmissive tube 206, in accordance with another alternative embodiment of the present inventors. In FIG. 10 and referring back to like elements shown in FIGS. 2-5, another alternate example of a system for the ultraviolet (UV) treatment of liquids or gases is described. The system includes a lamp 202, which is encased within an inner sleeve 204. The inner sleeve 204 is itself enclosed in a transmissive tube 206 (or a protective layer); and the transmissive tube 206 is disposed within a treatment chamber 208. The treatment chamber 208 has a reflective material 210 interposed between the transmissive tube 206 and the treatment chamber 208. In this example, the reflective material 210 is disposed on the outer surface of the transmissive tube 206 forming a reflective surface. Alternatively, the reflective material 210 may be attached to the transmissive tube 206 or the reflective material 210 may be a freestanding structure. Other placements and configurations for the reflective material 210 are possible. A liquid or gas 212 passes through the transmissive tube 206. In one example, the treatment chamber 208 is at least 80 percent enclosed.

The transmissive tube 206 runs through the chamber 208 where it is exposed to ultraviolet light provided by the ultraviolet lamp 202. The tube 206 may carry any type of liquid or gas 212, including for example, water, air, experimental reagents, blood components, e.g., red blood cells, white blood cells, plasma, beverages for consumption, and the like. Therefore, as the liquid or gas 212 passes through the ultraviolet transmissive tube 206, the liquid 212 (or gas) is exposed to ultraviolet photons useful for treating the liquid or gas 212 (and/or items within the liquid or gas 212). A UV monitor 220 monitors the level of UV radiation in the treatment chamber 208.

The treatment chamber 208 has an input port 214 and an output port 216 that allow for the ultraviolet transmissive tube 206 to run through the chamber 208. In other examples, the roles of the input port 214 and output port 216 are reversed. The input port 214 and the output port 216 are fashioned as such to render the chamber 208 as substantially enclosed as possible. For example, the input port 214 and/or output port 216 may utilize elbow, coiled, or other serpentine paths for gas and/or liquid flow to increase enclosure of the chamber 208. To further enhance enclosure, the flow path may be constricted to a smaller diameter and/or the reflective material 210 may be extended to a distance beyond the zone in which light is introduced. Additionally, additional structures such as baffles may also be incorporated into the apparatus to optimize chamber concealment. In any case, any number and combination of the aforementioned techniques, structures, and devices may be used to increase chamber enclosure.

Although the chamber 208 depicted in FIGS. 2-5 is coated with a reflective material 210, understood is that any type of reflective material 210 or reflective structure may be used. For example, the reflective material 210 which may be coated or lined on the inside of the chamber 208 may comprise at least one material, such as polytetrafluoroethylene (PTFE), expanded polytetrafluoroethylene (ePTFE), or other similar plastics, and may be coated, anodized, or polished aluminum. In another example, the reflective material 210 may be a reflector such as a diffuse or specular reflector. Any type of specular reflector, in any type of shape, may be used with the present example. In many examples, the reflective material 210 has a high level of reflectivity. For instance, the reflectivity level of the reflective material 210 may be in the range of 80 percent to 100 percent, and some approaches are 90 percent to 100 percent.

Although the exact percent reflectivity of the reflective material 210 may change depending on the particular needs of an apparatus, it should be understood that the higher the reflectivity, the higher the efficiency of the treatment chamber 208. For example, a fully enclosed chamber comprising a material with a 90 percent reflectivity in comparison to a fully enclosed chamber comprising a reflective material with a 99 percent reflectivity will have a lower dose on the target. Assuming that the exemplary target and walls are the only absorbers in the chamber, on average a photon will be reflected back and forth 10 times more in the 99 percent reflective chamber than the 90 percent reflective chamber before being absorbed by the reflective material. Thus, the photons are 10 times more likely to be absorbed by the target in a 99 percent reflective chamber than the 90 percent reflective chamber when the chamber is entirely enclosed.

Therefore, the 99 percent reflective chamber delivers 10 times the ultraviolet light dose on the target as the 90 percent reflective chamber.

Similarly, a 99 percent enclosed chamber will deliver a higher ultraviolet light dose on a target than a 90 percent enclosed chamber. In a less enclosed chamber, photons are more likely to be reflected out of the chamber, thus reducing the likelihood of the photons being absorbed by the target. As such, the dosage of ultraviolet light treatment ultimately delivered to a target material is inversely related to absorbance where reflectivity of the apparatus components and enclosability of the chamber affects absorbance.

The ultraviolet lamp 202 may be of any type useful for providing ultraviolet radiation. For example, low pressure mercury lamps, medium pressure mercury lamps, excimer lamps, flashlamps with xenon and other fill mixtures, and microwave-driven lamps may be used. Other examples of lamps are possible. In one example, the ultraviolet lamp 202 provides at least one wavelength less than 400 nm to a target for the deactivation or killing of biological materials therein. In another example, the ultraviolet lamp 202 provides at least one wavelength less than 400 nm to a target for the destruction of chemical compounds. The ultraviolet lamp 202 is connected to a power cable 224 in order to receive power. Additionally, end caps 22 may cover the ends of the lamp 202 to provide protection for the lamp 202. Furthermore, a lamp ballast 208 is also provided to, for example, limit current for the lamp 202.

Furthermore, an additional structure or layer exterior to the reflective material 210 may be provided to protect the reflective material 210, contain pressure, or both. Additionally, the transmissive tube 206 (or a protective layer) may contain system pressure.

As mentioned, the ultraviolet lamp 202 is enclosed by the inner sleeve 204, which allows a technician to change out the lamp 202 without opening the chamber 208. The inner sleeve 204 and the ultraviolet transmissive tube 206 may be of any material that is substantially transmissive to ultraviolet light. To achieve maximum efficiency of the treatment chamber 208, in some approaches, the material used for the inner sleeve 204 and the transmissive tube 206 is near 100 percent transmissivity as possible. In cases where 100 percent transmissivity is not possible, materials, such as fused silica (Heraeus Heralux, Momentive 214), synthetic quartz (Heraeus Suprasil, Momentive 021 and 022), fluorine doped silica (Asahi Glass AQX), and sapphire (Saphikon EFG sapphire), being generally higher than 80 percent transmissive in the wavelengths below 300 nm, are useful.

Due to the high reflectivity of the reflective material 210 in the present example, the vast majority of the ultraviolet photons are deposited into the liquid or gas (and/or to items within the liquid or gas 212) instead of the walls of the chamber 208. Consequently, the liquid or gas 212 (and/or items in the liquid or gas 212) receive a higher effective dose of radiation for a given input power.

Due to the lack of losses in other parts of the system, the upper limit to the number of photons that are absorbed by the liquid or gas 212 (and/or items within the liquid or gas 212) is multiplied by a factor roughly equal to the ratio of losses of the wall material of the chamber 208, e.g., as low as 1 percent, to that of stainless steel, e.g., 40 percent. The exact increase in UV dosage is affected by a variety of factors such as the number and size of penetrations into the volume containing the ultraviolet lamp 202 and liquid or gas 212, and any other disruptions in the surface of the reflective material 210. The overall increase in dosage over previous semi-reflective chambers, e.g., stainless steel chambers, is significant.

As mentioned, increased fluence may also be achieved due to a better reflector or reflective surface when using highly transmissive liquids. In this case, a substantial of the surface area, e.g., greater than 80%, surrounding the liquid is highly reflective.

In still other examples, increased uniformity and increased fluence are achieved. If the transmissivity of the liquid is substantially high, the increase in uniformity may occur but does impact performance as much as the increased fluence.

The increased dosage described above is accompanied by an unexpected increase in uniformity of the dose throughout the chamber, when compared to a system with a semi-reflective chamber wall. Normally, with higher fluence, a decrease in uniformity is expected, but the effect of minimizing the photon losses other than within the target gas or liquid produces a more uniform deposition of those photons within the target. This effect is essentially independent of geometry and primarily depends on the total reflectivity of the chamber walls or enclosure and on the transmissivity of the components involved.

A separate uniformity-enhancing effect which occurs for a different reason than the one above arises under certain conditions in this chamber. This effect is dependent upon the geometry of the chamber. It is also important only over a range of transmissivities of the liquid or gas 212. If the transmissivity of the liquid or gas 212 exceeds 90-95% (attenuation of 5-10%) over the distance from the light source to the chamber wall, then the effect described above does much more to create an unexpected uniformity of fluence in the chamber, and the effect described below is negligible. If the transmissivity is less than 5-10% (attenuation of 90-95%) over the distance from the light source to the chamber wall, then a very small amount of light reaches the chamber wall and once again the effect described below is negligible. For the range of transmissivities in the liquid or gas 212 such that the attenuation falls between nominally 5% and 95%, the effect described below is important in providing more uniform fluence to the target.

Further, the ultraviolet irradiance provided by the present approaches may fall into a variety of different ranges. In one example, the ultraviolet irradiance impinging on the liquid is in a range of approximately 0.01 W/cm$^2$ to approximately 20 W/cm$^2$. Other examples of ranges are possible.

Referring back to FIGS. 6-8 in relation to FIG. 10, the light absorption properties of the some present are herein described. The intensity of light which is transmitted through an absorbing medium is governed by Beer's Law:

$$I = I_o e^{-\alpha x}$$

where $I_o$ is the initial intensity, x is the distance traveled through the absorbing medium, e is the base of natural logarithms (e=2.718282), and $\alpha$ is an attenuation constant determined by the characteristics of the medium. If the medium and its dimensions are such that only a significant fraction of the light is absorbed after a single pass through the medium, then the effect shown in FIGS. 6-8 occurs.

Information as herein shown and described in detail is fully capable of attaining the above-described object of the invention, the presently preferred embodiment of the invention, and is, thus, representative of the subject matter which is broadly contemplated by the present invention. The scope of the present invention fully encompasses other embodiments which may become obvious to those skilled in the art, and is to be limited, accordingly, by nothing other than the appended claims, wherein reference to an element in the singular is not intended to mean "one and only one" unless explicitly so stated, but rather "one or more." All structural and functional equivalents to the elements of the above-described preferred embodiment and additional embodiments that are known to those of ordinary skill in the art are hereby expressly incorporated by reference and are intended to be encompassed by the present claims.

Moreover, no requirement exists for a device or method to address each and every problem sought to be resolved by the present invention, for such to be encompassed by the present claims. Furthermore, no element, component, or method step in the present disclosure is intended to be dedicated to the public regardless of whether the element, component, or method step is explicitly recited in the claims. However, that various changes and modifications in form, material, and fabrication material detail may be made, without departing from the spirit and scope of the invention as set forth in the appended claims, should be readily apparent to those of ordinary skill in the art. No claim herein is to be construed under the provisions of 35 U.S.C. §112, sixth paragraph, unless the element is expressly recited using the phrase "means for."

INDUSTRIAL APPLICABILITY

The present invention industrially applies to the treatment of fluids using ultraviolet light. More specifically, the present invention industrially applies to the treatment of fluids using ultraviolet light. Even more specifically, the present invention industrially applies to the treatment of fluids using ultraviolet light for deactivating microorganisms.

What is claimed:
1. An apparatus for the treatment of a liquid comprising:
a chamber being enclosed by at least one wall having at least one inner surface, the inner surface of the at least one wall enclosing the chamber;
an ultraviolet lamp, the ultraviolet lamp being disposed within the chamber, the ultraviolet lamp producing ultraviolet photons;
an ultraviolet transmissive tube including an interior and a continuous interior-facing surface surrounding the interior, the ultraviolet transmissive tube being made of a material that is transmissive to ultraviolet light, the ultraviolet transmissive tube being disposed within the chamber and adapted to permit a fluid to pass through the chamber by flowing through the interior of the ultraviolet transmissive tube, wherein the fluid within the chamber is fully contained by the interior-facing surface within the ultraviolet transmissive tube, the ultraviolet transmissive tube having an outer surface that faces the inner surface of the at least one wall enclosing the chamber;
a reflective surface enveloping the ultraviolet lamp by at least 80 percent; the reflective surface adapted so as to reflect at least a portion of light emitted by the ultraviolet lamp, wherein the reflective surface is at least 80 percent reflective, wherein the reflective surface is disposed on the outer surface of the ultraviolet-transmissive tube;
wherein enveloping of the lamp by at least 80 percent and the reflectivity of the reflective surface being at least 80 percent are effective to deposit a majority of the ultraviolet photons within a volume of the fluid;
wherein the ultraviolet lamp is disposed within a transmissive protective sleeve within the ultraviolet-transmissive tube.

2. The apparatus of claim 1, wherein the confluence of the first light from the ultraviolet lamp and second light and subsequent light reflected from the reflective surface produce an unexpectedly generally uniform light distribution to occur within the volume of the fluid.

3. The apparatus of claim 2, wherein the fluid is highly transmissive and a heightened fluence is achieved in the fluid.

4. The apparatus of claim I, wherein the reflective surface comprises a reflective material comprising at least one material selected from a group consisting essentially of polytetrafluoroethylene (PTFE), expanded polytetrafluoroethylene (ePTFE), coated aluminum, anodized aluminum, and polished aluminum.

5. The apparatus of claim 1, wherein the reflective surface comprises a reflective material comprising a mixture, the mixture comprising of a binder and a reflective additive.

6. The apparatus of claim 5, wherein the reflective additive comprises at least one material selected from a group consisting essentially of barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, and zirconium oxide.

7. The apparatus of claim 1, further comprising an input port and an output port, wherein the ultraviolet-transmissive tube enters and exits the chamber.

8. The apparatus of claim 1, wherein an ultraviolet irradiance impinging on the fluid comprises a range of approximately 0.01 W/cm$^2$ to approximately 20 W/cm$^2$.

9. An apparatus for the treatment of a liquid comprising:
a chamber being enclosed by at least one wall having at least one inner surface, the inner surface of the at least one wall enclosing the chamber;
an ultraviolet lamp, the ultraviolet lamp being disposed within a transmissive protective sleeve that is disposed within the chamber, the ultraviolet lamp producing ultraviolet photons;
an ultraviolet transmissive tube disposed within the chamber, the ultraviolet transmissive tube having an outer surface that faces the inner surface of the at least one wall enclosing the chamber, the ultraviolet transmissive tube including an interior and a continuous interior-facing surface surrounding the interior, the ultraviolet transmissive tube being made of a material that is transmissive to ultraviolet light, the ultraviolet transmissive tube being disposed within the chamber and adapted to permit a fluid to pass through the chamber by flowing through the interior of the ultraviolet transmissive tube, wherein the fluid within the chamber is fully contained b the interior-facing surface within the ultraviolet transmissive tube;
a reflective surface enveloping the ultraviolet lamp by at least 80 percent, the reflective surface adapted so as to reflect at least a portion of light emitted by the ultraviolet lamp, wherein the reflective surface is at least 80 percent reflective, wherein the reflective surface is disposed on the outer surface of the ultraviolet-transmissive tube; and
wherein the confluence of the first light from the ultraviolet lamp and second light and subsequent light reflected from the reflective surface produce a generally uniform light distribution to occur within a volume of the fluid and wherein enveloping of the lamp by at least 80 percent and the reflectivity of the surface being at least 80 percent are effective to deposit a majority of the ultraviolet photons within the volume of the fluid.

10. The apparatus of claim 9, wherein the transmissivity of the liquid is such that its attenuation falls in a range of approximately 5 percent to approximately 95 percent.

11. The apparatus of claim 9, wherein the reflective surface comprises a reflective material comprising at least one material selected from a group consisting essentially of polytetrafluoroethylene (PTFE), expanded polytetrafluoroethylene (ePTFE), coated aluminum, anodized aluminum, and polished aluminum.

12. The apparatus of claim 9, wherein the reflective material comprises a reflective material comprising a mixture, the mixture comprising a binder and a reflective additive.

13. The apparatus of claim 12, wherein the reflective additive comprises at least one material selected from a group consisting essentially of barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, and zirconium oxide.

14. The apparatus of claim 9, further comprising an input port and an output port, wherein the ultraviolet-transmissive tube enters and exits the chamber.

15. The apparatus of claim 9, wherein an ultraviolet irradiance impinging on the fluid comprising a range of approximately 0.01 W/cm$^2$ to approximately 20 W/cm$^2$.

* * * * *

UNITED STATES PATENT AND TRADEMARK OFFICE
CERTIFICATE OF CORRECTION

PATENT NO. : 9,808,544 B2  
APPLICATION NO. : 12/416075  
DATED : November 7, 2017  
INVENTOR(S) : Cooper et al.

Page 1 of 1

It is certified that error appears in the above-identified patent and that said Letters Patent is hereby corrected as shown below:

In the Claims  
Claim 1, Column 19, Line 58, delete "percent;" and insert --percent,--.  
Claim 4, Column 20, Line 12, delete "claim I," and insert --claim 1,--.  
Claim 9, Column 20, Line 55, delete "b" and insert --by--.

Signed and Sealed this  
Thirteenth Day of March, 2018

Andrei Iancu  
*Director of the United States Patent and Trademark Office*